(12) United States Patent
Greenfield et al.

(10) Patent No.: US 7,767,646 B2
(45) Date of Patent: Aug. 3, 2010

(54) METHODS OF SCREENING FOR COMPOUNDS THAT MODULATE TAFIA ACTIVITY, COMPOUNDS, AND METHODS OF USING THE COMPOUNDS

(75) Inventors: Robert S. Greenfield, Trumbull, CT (US); Seong Soo A. An, Hopewell Junction, NY (US); Latchezar Trifonov, Montreal (CA); Jean Vaugeois, Verdun (CA); Clarke Slemon, Portland (CA)

(73) Assignee: American Diagnostica, Inc., Stamford, CT (US)

( * ) Notice: Subject to any disclaimer, the term of this patent is extended or adjusted under 35 U.S.C. 154(b) by 691 days.

(21) Appl. No.: 11/544,906

(22) Filed: Oct. 6, 2006
(Under 37 CFR 1.47)

(65) Prior Publication Data

US 2008/0305508 A1 Dec. 11, 2008

Related U.S. Application Data

(62) Division of application No. 10/651,659, filed on Aug. 29, 2003, now Pat. No. 7,119,068.

(60) Provisional application No. 60/407,138, filed on Aug. 29, 2002, provisional application No. 60/407,395, filed on Aug. 30, 2002.

(51) Int. Cl.
*C12Q 1/00* (2006.01)
(52) U.S. Cl. ............................................. 514/12; 435/4
(58) Field of Classification Search ........................ None
See application file for complete search history.

(56) References Cited

U.S. PATENT DOCUMENTS

2003/0035795 A1 2/2003 Gardell et al.

FOREIGN PATENT DOCUMENTS

WO WO 03/061653 7/2003

OTHER PUBLICATIONS

American Society of Hematology, Novel Fibrinolytic Action Of Aspirin Identified, Dec. 6-10, 2002, Philadelphia, PA.
Itami et al., (J. Org. Chem. (1998) vol. 63, p. 6466-6471.

*Primary Examiner*—Brandon J Fetterolf
(74) *Attorney, Agent, or Firm*—Frommer Lawrence & Haug LLP

(57) ABSTRACT

Provided are methods of screening compounds for any aspirin-related activity other than TAFI inhibition, and also for non-inhibition of TAFI. Compounds identified by the screening methods can be used to treat, prevent or manage in a patient pain, fever, colon cancer, pancreatic cancer or an inflammatory, platelet aggregation, fibrinolytic or hemorrhagic disease or disorder. Also provided is a method of evaluating test compounds for TAFI inhibitory activity wherein the TAFI inhibitory activity of these test compounds is compared to the TAFI inhibitory activity of aspirin or its derivatives or metabolites. Further provided is a method of treating, preventing or managing in a patient, a hemorrhagic or thrombotic disease or disorder with high dose aspirin or aspirin derivatives or metabolites. Also contemplated is a method of treating, preventing or managing in a patient, pain, fever, colon cancer, pancreatic cancer or an inflammatory, platelet aggregation, fibrinolytic or hemorrhagic disease or disorder comprising administering aspirin or a derivative thereof or any other therapeutic having at least one desired therapeutic or prophylactic activity of aspirin to a patient in need thereof and administering to the patient a factor that promotes TAFIa activity, e.g. stabilized TAFIa, to ameliorate one or more adverse side effects of the therapeutic. Compounds identified by the methods of the invention are also provided.

9 Claims, 10 Drawing Sheets

METHODS OF SCREENING FOR COMPOUNDS THAT MODULATE TAFIA ACTIVITY, COMPOUNDS, AND METHODS OF USING THE COMPOUNDS

CROSS-REFERENCE TO RELATED APPLICATIONS

This application is a divisional of U.S. application Ser. No. 10/651,659 filed Aug. 29, 2003, now U.S. Pat. No. 7,119,068, which claims priority to U.S. application Ser. No. 60/407,138, filed on Aug. 29, 2002 and to U.S. application Ser. No. 60/407,395, filed on Aug. 30, 2002.

The foregoing applications, as well as all documents cited in the foregoing applications ("application documents") and all documents cited or referenced in the application documents are hereby incorporated by reference. Also, all documents cited in this application ("herein-cited documents") and all documents cited or referenced in the herein-cited documents are incorporated by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The invention relates to the general field of fibrinolysis. One aspect of the invention relates to methods of screening compounds for any aspirin-related activity other than TAFI inhibition, e.g., analgesia, fever reduction, anti-inflammation, anti-platelet aggregation, colon cancer prophylaxis, pancreatic cancer prophylaxis, but for non-inhibition of TAFI. A second aspect of the invention encompasses utilizing the compounds identified by the screening methods of the invention to treat, prevent or manage in a patient pain, fever, colon cancer, pancreatic cancer or an inflammatory, platelet aggregation, fibrinolytic or hemorrhagic disease or disorder. A third aspect of the invention relates to a method of evaluating test compounds for TAFI inhibitory activity wherein the TAFI inhibitory activity of these test compounds is compared to the TAFI inhibitory activity of aspirin or its derivatives or metabolites. A fourth aspect of the invention comprises a method of treating, preventing or managing in a patient, a hemorrhagic or thrombotic disease or disorder with high dose aspirin or aspirin derivatives or metabolites, including but not limited to salicylic acid, salicylic acid, gentisic acid, glycyl amides and α-hydroxybenzoate derivatives. A fifth aspect of the invention relates to a method of treating, preventing or managing in a patient, pain, fever, colon cancer, pancreatic cancer or an inflammatory, platelet aggregation, fibrinolytic or hemorrhagic disease or disorder comprising administering aspirin or a derivative thereof or any other therapeutic having at least one desired therapeutic or prophylactic activity of aspirin to a patient in need thereof and administering to the patient a factor that promotes TAFIa activity, e.g. stabilized TAFIa, to ameliorate one or more adverse side effects of the therapeutic. A sixth aspect of the invention relates to compounds identified by the methods of the invention.

BACKGROUND OF THE INVENTION

Aspirin and its Activities

A proper balance between the activities of coagulation and fibrinolytic cascades is needed both to protect an organism from excessive blood loss upon injury and to maintain blood flow within the vascular system. The two opposing coagulation and fibrinolytic cascades are recognized to comprise a series of zymogen to enzyme conversions which terminate in the two respective proteolytic enzymes, thrombin and plasmin. These enzymes catalyze the formation and removal of fibrin within the circulatory system. Imbalances are characterized by either bleeding or thrombotic tendencies which may result in heart attacks or strokes in the organism.

The anti-thrombotic effect of aspirin has long been recognized, and low doses of aspirin (acetylsalicylic acid; ASA) are recommended for the prevention of ischemic events in patients with coronary artery disease. In large clinical studies, aspirin has been shown to significantly reduce both the occurrence of myocardial infarction and mortality rate in patients with unstable angina pectoris that often occurs before a heart attack and/or previous myocardial infarction. Simoons, M., *Lancet*, 2001, 357(9272):1915-24.

The action of aspirin as well as other non-steroidal anti-inflammatory drugs (NSAIDS) is thought to derive mostly from the selective inhibition of cyclooxygenase 1 and 2 (COX-1 and -2). At the platelet-vessel wall, aspirin at low doses selectively and irreversibly inhibits COX-1, which synthesizes thromboxane A2 (Tx-A2) and causes platelet activation. Hence, aspirin prevents blood platelets from aggregating, one of the initial steps in the formation of blood clots.

Aspirin is also a currently available therapy for several other diseases and disorders including fever, colon cancer, pancreatic cancer and inflammatory diseases such as arthritis. Aspirin is often a first-line therapy for rheumatoid arthritis, an inflammatory process which causes erosion or destruction of bone and cartilage joints. In addition to aspirin, current arthritis treatment regimens often employ ibuprofen and COX-2 inhibitors such as CELEBREX® (celecoxib) and VIOXX® (rofecoxib) which also act by reducing inflammation of the joints. Although these treatments are well established for arthritis sufferers, they often have unwanted or adverse side effects.

Thus, while aspirin and other drugs are often used for their known analgesic activity, antipyretic activity, anti-inflammatory activity, anti-platelet aggregation activity and prophylactic properties, aspirin's mechanism of action, and concomitantly, the mechanisms that lead to the production of unwanted side effects, are not yet fully understood. For example, the anti-platelet activity of aspirin cannot account for all the biological effects associated with aspirin therapy. Aspirin has been shown to reduce thrombin generation at the site of injury and can effect tissue factor-initiated coagulation. Undas et al., 2001, *Blood*, 98:2423-2431. Other studies suggest that aspirin therapy increases the fibrinolytic activity of plasma. Green, D., 2001, *Clin. Cornerstone*, 3:50-60. Further studies have been unable to attribute the mechanism by which aspirin enhances fibrinolysis to changes in tissue plasminogen activator levels. Bjomsson et al., 1989, *J. Pharmacol. Exp. Ther.*, 250:154-161. Thus, there is confusion in the art regarding the mechanism of aspirin action, particularly in causing adverse side effects.

Thrombin Activatable Fibrinolysis Inhibitor

Thrombin activatable fibrinolysis inhibitor ("TAFI") is a 60 kDa glycoprotein present in human plasma that modulates fibrinolysis in vivo. TAFI present in plasma is a proenzyme form which is most efficiently activated by proteolytic cleavage at Arg-92 with a thrombin-thrombomodulin complex. TAFI may also be activated by proteolytic cleavage by other proteolytic enzymes including, but not limited to, thrombin or plasmin ("activation of TAFI"). Upon activation of TAFI by proteolytic cleavage with thrombin-thrombomodulin, an active enzyme of 35 kDa is formed with carboxypeptidaselike activity ("TAFIa"). This molecule has also been referred to in the literature as plasma carboxypeptidase B ("PCPB"), or plasma carboxypeptidase U ("PCPU"). Tan et al., *Biochemistry*, 1995, 34:5811-5816; Wang et al., *J. Biol. Chem.* 269:15937 (1994); Nesheim et al., 1995, *J. Biol. Chem.* 270: 14477.

Modulation of fibrinolysis occurs when TAFIa cleaves C-terminal arginine and lysine residues of partially degraded fibrin, thereby inhibiting the stimulation of tissue plasminogen activator (t-PA) modulated plasminogen activation. The fibrinolytic system is activated primarily by t-PA which is provided by damaged cells in the blood vessel wall. t-PA converts circulating plasminogen to the active protease plasmin and can produce either slow enhancement of fibrinolysis or, when combined with fibrin, rapid enhancement of fibrinolysis. The effect of t-PA on fibrinolysis can be blocked by a class of inhibitors termed plasminogen activator inhibitors (PAIs), of which several have been identified.

Thrombomodulin is a component of the blood vessel wall which binds thrombin and changes its specificity from fibrinogen to protein C, resulting in a molecule possessing anticoagulant, rather than procoagulant, activity. The thrombin-thrombomodulin complex catalyzes cleavage of protein C to activated protein C, which results in down-regulation of the coagulation cascade by proteolytically inactivating the essential cofactors, Factor Va and VIIIa. In this manner, the body regulates coagulation cascade.

Studies such as that by Taylor et al., 1985, *Thromb. Res.* 37:639 have suggested that activated protein C is not only an anticoagulant, but also profibrinolytic, both in vivo and in vitro. Subsequently, it was determined that protein C only appears profibrinolytic because it prevents the thrombin-catalyzed activation of a previously unknown fibrinolysis inhibitor, whose precursor was isolated from plasma and designated as being TAFI.

TAFI was discovered independently in three different laboratories. It initially appeared as an unstable carboxypeptidase B-like molecule in human serum and was described by Hendriks et al., 1990, *Biochim. Biophys. Acta* 1014:86. A year later the cDNA for the molecule was cloned, its amino acid sequence was described, its activation by trypsin and its enzymatic properties toward synthetic carboxypeptidase B substrates was reported (see U.S. Pat. No. 5,206,161). In 1994, Wang et al., (1994, *J. Biol. Chem.* 269:15937) isolated the activated molecule and named it carboxypeptidase U ("U" being designated for unstable). Subsequently, Nesheim et al. (1995, *J. Biol. Chem.* 270:14477) showed that the protein was both activated by thrombin and inhibits fibrinolysis, and designated the molecule TAFI. The co-identity of PCPB, PCPU, and TAFI has been established by their independent chromatographic behavior on plasminogen Sepharose® and the amino acid sequences present at the activation cleavage site.

The mechanism of TAFI inhibition of fibrinolysis can be schematically described as depicted in FIG. 5.

As TAFIa is believed to play a central regulatory role in the fibrinolytic cascade, the manipulation of TAFIa levels or activity in biological fluids has important therapeutic applications with respect to hemorrhagic disorders including, but not limited to, vascular and heart pathologies, and stroke. Inhibitors of TAFIa enhance fibrinolysis and have an anticoagulant effect (see U.S. Pat. No. 5,993,815). Inhibitors of TAFIa could also be effective at treating or preventing the inflammation associated with arthritis as vascular endothelial growth factor (VEGF) is a potential substrate of TAFIa. VEGF has been linked with arthritis (Farva, R. A., 1994, *J. Exp. Med.* 180:341-6).

There remains a need in the art for methods of modulating TAFIa activity for therapeutic use in the treatment, prevention or management of hemorrhagic or thrombotic diseases or disorders. Moreover, there is a need to identify compounds that have the analgesic, antipyretic activity, anti-inflammatory activity, anti-platelet aggregation activity and prophylactic activity of aspirin without the hemorrhagic side effects. In addition there remains a need in the art for effective methods of screening compounds for TAFIa modulating activity which may be used in the treatment of fibrinolytic or thrombotic diseases or disorders.

SUMMARY OF THE INVENTION

The present invention is based, in part, on the surprising discovery that aspirin and two of its derivatives, salicylic acid ("SA") and salicyluric acid ("SU"), promote fibrinolysis by inhibiting TAFIa enzymatic activity and, in the case of salicylic acid and salicyluric acid, by inhibiting activation of TAFI, i.e., the conversion of TAFI proenzyme to TAFIa. The present inventors have identified the mechanism mediating aspirin's hemorrhagic side effects, and thus a novel target for aspirin action. In brief, the present invention relates to methods for diagnostic and/or therapeutic use of TAFIa inhibitors, and methods of screening and modeling compounds for TAFIa inhibitory activity, or lack thereof, and other aspirin activities, or lack thereof. The invention further relates to compounds identified by the methods of screening discovered by the inventors.

The compounds screened and identified by the methods of the invention can be of the general formula of Structure I:

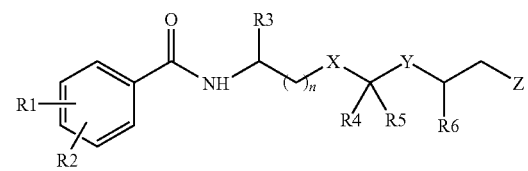

where

R1 is H, OH, alkoxy, aralkyloxy, $NH_2$, acylamino or $CH_2N(alkyl)_2$;

R2 is H, OH, alkoxy, aralkyloxy, $NH_2$, acylamino or $CH_2N(alkyl)_2$;

R3 is H, aryl or aralkyl;

R4 is H or R4+R5 is O or NH;

R5 is H or R4+R5 is O or NH;

R6 is H or COOH;

X is $CH_2$, NH or O;

Y is $CH_2$, NH or O;

Z is $(CH_2)_nNH_2$, NHCOAr, $NHC(=NH)NH_2$, $(CH_2)_pNHC(=NH)NHSO_2Aryl$, $C(=NH)NH_2$ or $S_2(CH_2)_2NH_2$;

n is 1, 2, 3, 4, 5 or 6;

m is 1, 2, 3, 4, 5 or 6; and p is 0, 1, 2 or 3.

The compounds screened and identified by the methods of the invention can also be of the general formula of Structure II:

where:
- R1 is H, OH, alkoxy, aralkyloxy, $NH_2$, acylamino or $CH_2N(alkyl)_2$;
- R2 is H, OH, alkoxy, aralkyloxy, $NH_2$, acylamino or $CH_2N(alkyl)_2$;
- R3 is alkyl, aryl or aralkyl;
- R4 is OH or COOH; and
- n is 0, 1, 2, 3, 4 or 5.

The compounds screened and identified by the methods of the invention can also be of the general formula of Structure III:

where:
- R1, R, R5, R6 is H, OH, alkoxy, aralkyloxy, $NH_2$, acylamino or $CH_2N(alkyl)_2$;
- R3 is H or R3+R4=O or NH;
- R4 is H or R3+R4=O or NH;
- X is O, NH or $CH_2$;
- Y is O, NH or $CH_2$;
- n is 0, 1, 2, 3 or 4; and
- m is 0, 1, 2, 3 or 4.

In one embodiment of the invention, compounds are screened for both aspirin activities and non-inhibition of TAFIa, to identify compounds with the more beneficial activities of aspirin, but without certain unwanted or adverse side effects, e.g. bleeding. These compounds can be used at higher doses and/or longer time periods than aspirin and its derivatives, since these unwanted or adverse side effects of aspirin would be eliminated. In one embodiment, a test compound is screened for COX-1 and/or COX-2 activity and for non-inhibition of TAFIa. In another embodiment, test compounds are screened for at least one aspirin activity selected from the group consisting of analgesia, fever reduction, anti-inflammation, anti-platelet aggregation, colon cancer prophylaxis, pancreatic cancer prophylaxis and thrombotic disease prophylaxis, and for non-inhibition of TAFIa activity and/or non-inhibition of TAFI activation. In another embodiment, test compounds are screened for more than one aspirin activity, other than inhibition of TAFI activation or TAFIa activity, selected from the group consisting of analgesia, anti-inflammation, anti-platelet aggregation, fever reduction, colon cancer prophylaxis, pancreatic cancer prophylaxis and thrombotic disease prophylaxis, and for non-inhibition of TAFIa activity and/or non-inhibition of TAFI activation.

Another aspect of the invention is directed to methods of screening compounds for TAFIa inhibitory activity and/or inhibition of TAFI activation. In a particular embodiment, TAFIa inhibitory activity of the test compound is compared to that of aspirin, salicylic acid, salicyluric acid or gentisic acid. Test compounds can be screened for TAFIa inhibitory activity and for non-inhibition of aspirin activity.

A further aspect of the invention involves compounds identified by the methods of screening. In particular, several compounds have been identified that have TAFIa inhibitory activity. One of these is the compound designated L278R, having the following structure:

Another compound of the invention is designated. LT32, and has the following structure:

A further compound of the invention is designated JV59, and has the following structure:

Other aspects of the invention relate to methods of treating, preventing or managing pain, fever, inflammation, platelet aggregation, colon cancer or pancreatic cancer comprising administering a therapeutically or prophylactically effective amount of a compound identified by the screening methods of the invention to a patient in need thereof. A particular embodiment of the invention relates to a method of treating, preventing or managing hemorrhagic or thrombotic diseases or disorders comprising administering a therapeutically or prophylactically effective amount of a TAFIa modulator, or a pharmaceutically acceptable composition thereof, to a patient having such a disease or disorder. In preferred embodiments of the invention, aspirin-derived inhibitors of TAFIa include, but are not limited to salicylic acid, salicyluric acid, gentisic acid, glycyl amides and α-hydroxybenzoate derivatives.

A further aspect of the invention relates to limiting the adverse effects of aspirin therapy by administering a factor that promotes TAFIa activity, such as stabilized TAFIa. See U.S. patent application Ser. No. 10/116,095, filed Apr. 4, 2002. One embodiment of the invention relates to methods of treating, preventing or managing pain, fever, inflammation, platelet aggregation, colon cancer or pancreatic cancer comprising the steps of administering a therapeutically or prophylactically effective amount of aspirin or aspirin derivative or other anti-inflammatory to a patient in need thereof and administering to a patient an effective amount of stabilized TAFIa.

The compounds of the invention can be formulated into pharmaceutical compositions and administered in combination with another prophylactic or therapeutic agent. In certain embodiments, the other therapeutic or prophylactic agent is useful for the treatment, prevention or management of at least one of the following: pain, fever, inflammation, platelet aggregation, fibrinolysis or hemorrhage, colon cancer or pancreatic cancer. When used in combination with other prophylactic and/or therapeutic agents, the compound of the invention, or pharmaceutical composition thereof, can be administered prior to, subsequent to or concurrently with the other therapeutic or prophylactic agents. Additionally, agents used in combination may be administered in the same composition or in separate pharmaceutical compositions.

These and other aspects and features of the invention will be more fully appreciated when the following detailed description of the invention is read in conjunction with the accompanying figures.

BRIEF DESCRIPTION OF THE DRAWINGS

The following Detailed Description, given by way of example, but not intended to limit the invention to specific embodiments described, may be understood in conjunction with the accompanying drawings, incorporated herein by reference, in which:

FIG. 1 shows that TAFIa carboxypeptidase activity is inhibited in a dose-dependent manner by ASA, SA and SU. SU was the most effective inhibitor followed by SA and ASA.

FIG. 3 shows that TAFIa activity is inhibited in a dose-dependent manner by SA upon incubation at room temperature. About 60% TAFIa activity is lost at 25 mM SA.

DETAILED DESCRIPTION OF THE INVENTION

Definitions

Figure 1:
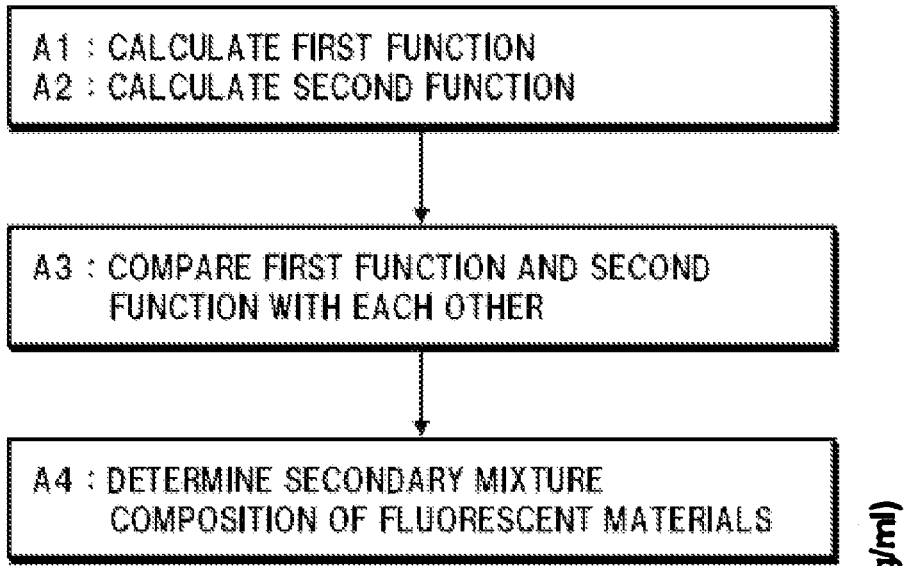
FIG. 1 shows the effect on TAFIa activity of incubation with various concentrations of salicylic acid ("SA") (open circles), salicyluric acid (2-hydroxyhippuric acid) ("SU") (closed squares) and acetylsalicylic acid (ASA) (closed circles) for 1 hour at room temperature. Residual TAFIa activity was measured using ActiFLUOR TAFIa.
Figure 1:
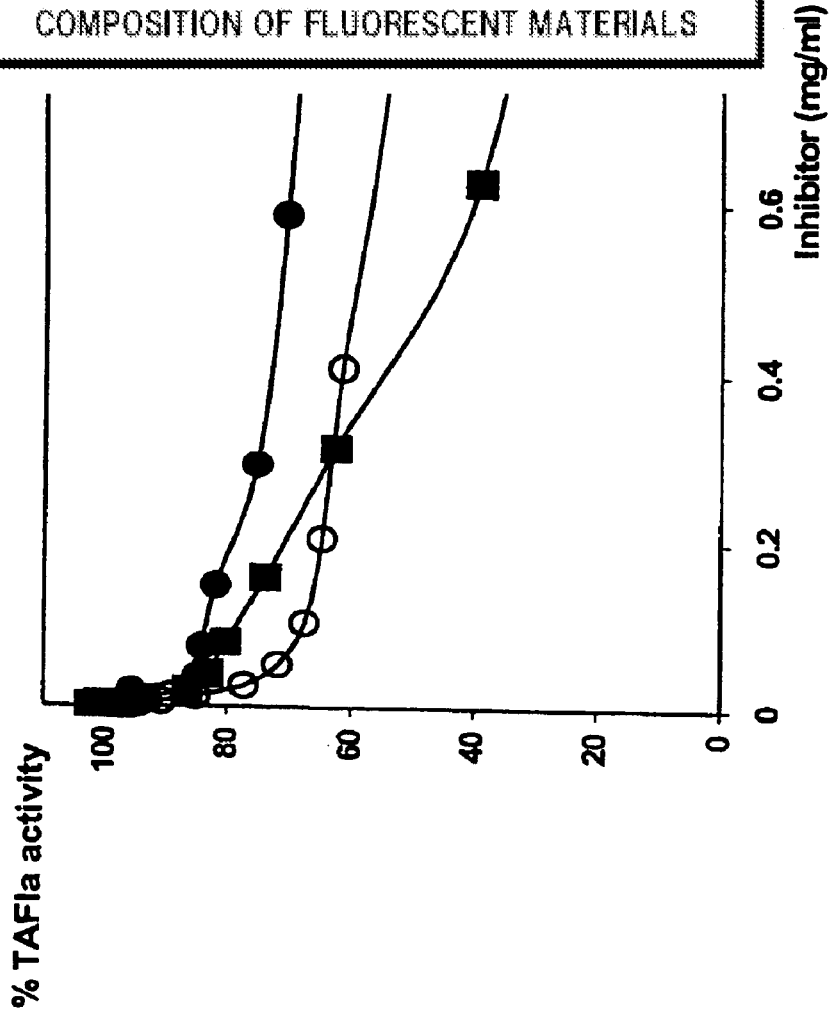
Figure 2:
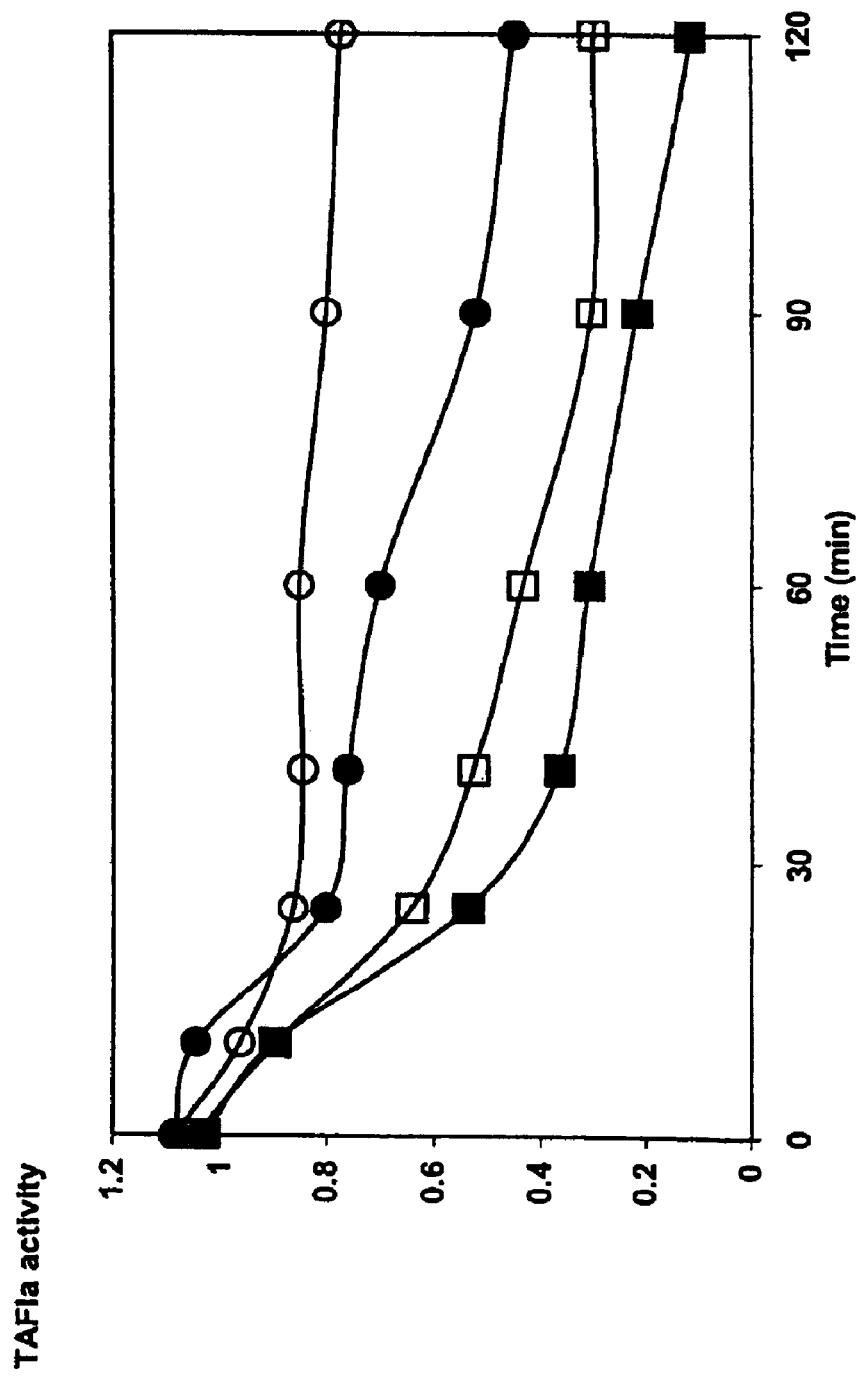
FIG. 2 shows the effect on TAFIa activity of incubation with different concentrations 0 µg (open circles), 200 µg (closed circles), 400 µg (open squares) and 800 µg (closed squares) of salicylic acid at 37° C., wherein aliquots were later removed and measured for TAFIa activity.
Figure 3:
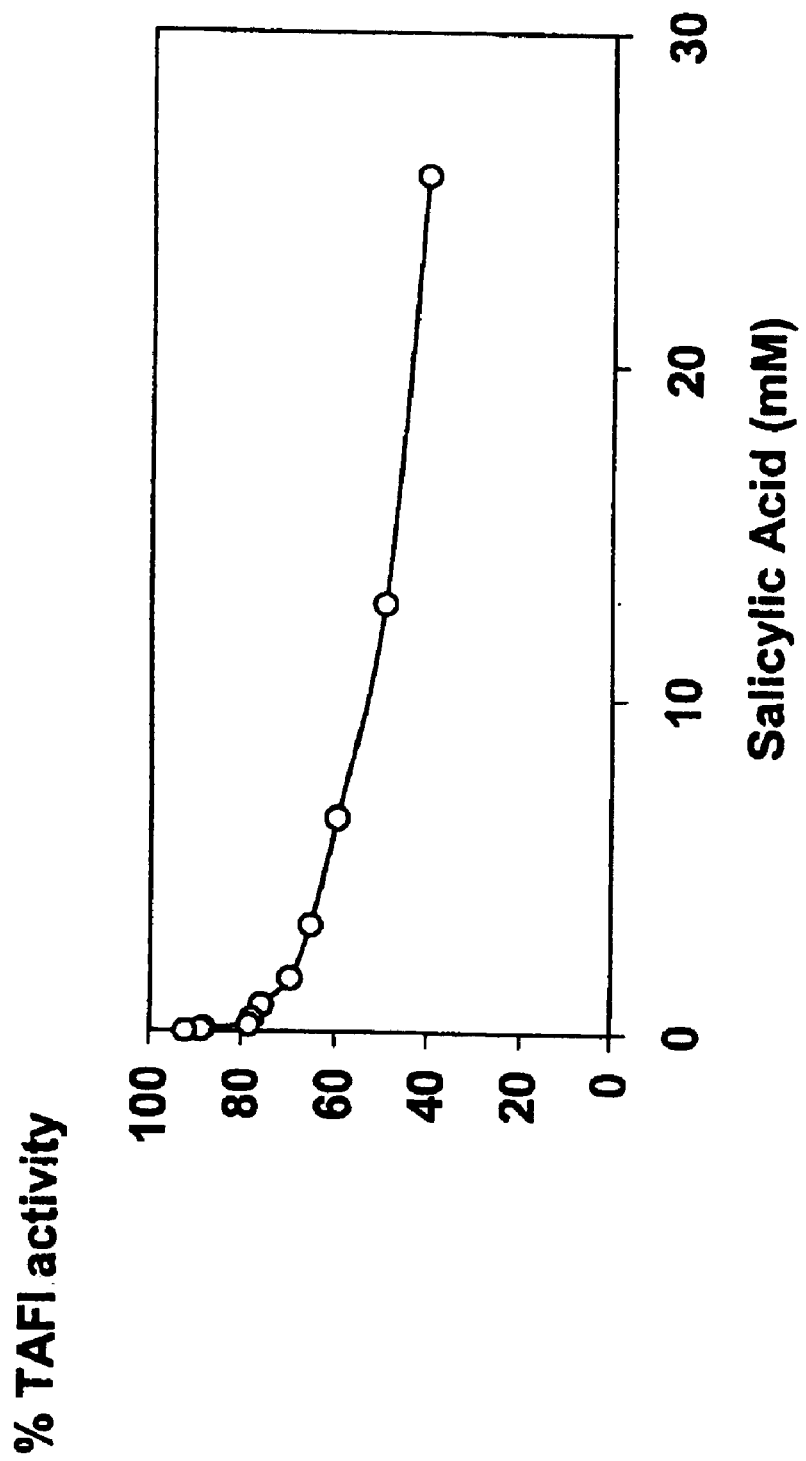
FIG. 3 shows the effect on TAFIa activity of incubation with various concentrations of salicylic acid at room temperature for 1 hour. Residual TAFIa activity was measured using ActiFLUOR TAFIa.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

The term "derivative" as used herein refers to a chemical compound related structurally to another chemical compound and therapeutically derivable from it. "Aspirin derivatives" or "derivatives of aspirin" include, but are not limited to salicylate, salicylatic acid, glucuronic acid, dihydroxyamids and salsalate (a dimer of salicylic acid). Additionally, derivatives of α-hydroxybenzoate are also contemplated by the instant invention, including but not limited to gentisic acid and glycyl amides.

The term "metabolite" as used herein refers to a chemical compound produced by chemical conversion of an administered chemical compound in a living organism.

The term "small molecule" as used herein refers to a molecule with a molecular weight less than 500.

The phrase "modulation of fibrinolysis" as used herein means the inhibition or activation of the fibrinolytic cascade which may have an anti-coagulant or procoagulant effect.

"TAFI inhibitor" or "inhibitor of TAFI" as used herein means any molecule that blocks, reduces or retards the activation of TAFI, i.e., any molecule that blocks, reduces or retards the cleavage of fibrin or other substrates by TAFIa, any molecule that blocks, reduces, or retards TAFIa enzymatic activity or any molecule that blocks, reduces or retards the cleavage of TAFI proenzyme to form TAFIa.

The phrase "stabilized TAFIa" as used herein means TAFIa that has a half-life of at least one hour at room temperature, more preferably of at least two hours, more preferably of at least four hours, more preferably of at least eight hours, more preferably of at least twelve hours, more preferably of at least twenty-four hours and most preferably of at least forty-eight hours. Prepared, e.g., using methods of U.S. patent application Ser. No. 10/116,095, filed Apr. 4, 2002.

The terms "disorder" and "disease" are used interchangeably to refer to a condition in a patient. In particular, the term "thrombotic disease" is used interchangeably with the term "thrombotic disorder" to refer to a condition in a patient characterized by undesired clot formation. In particular, the term "fibrinolytic disease" is used interchangeably with the term "fibrinolytic disorder" to refer to a condition in a patient characterized by enhanced or reduced dissolution of fibrin clot. In particular, the term "inflammatory disease" is used interchangeably with the term "inflammatory disorder" to refer to a condition in a patient characterized by inflammation, preferably chronic inflammation. One of skill in the art is capable of recognizing and diagnosing thrombotic, fibrinolytic and inflammatory diseases and disorders.

The term "pain" refers to all categories of pain, including pain that is described in terms of stimulus or nerve response, e.g., somatic pain (normal nerve response to noxious stimulus) and neuropathic pain (abnormal response of an injured or altered sensory pathway, often without clear noxious input); pain that is categorized temporally, e.g., chronic pain and acute pain; pain that is categorized in terms of severity, e.g., mild, moderate, or severe; pain that described in terms of origin or site of inflammation, e.g., peripheral nervous system or central nervous system; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see e.g., Harrison's Principles of Internal Medicine, pp. 93-98 (Wilson et al, eds., $12^{th}$ ed. 1991); Williams et al., *J. of Medicinal Chem.* 42:1481-1485 (1999).

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic" pain, as described above, refers to pain resulting from injury to or chronic changes in peripheral and/or central sensory pathways, where the pain often occurs or persists without an obvious noxious input.

The term "fever" as used herein refers to a patient's body temperature which is higher than 100.4° F. (38° C.) measured rectally, higher than 100° F. (37.8° C.) measured orally, or higher than 99° F. (37.2° C.) measured under the arm.

The term "inflammation" as used herein refers all categories of inflammation, including localized manifestations and systemic inflammation (e.g., caused by infection with bacteria, fungi, or viruses, e.g., endotoxin, polysaccharide or viral proteins respectively, by inflammatory mediators, or as a consequence of auto-immune disorders); inflammation that is categorized temporally, e.g., chronic inflammation and acute inflammation; inflammation that is categorized in terms of its severity, e.g., mild, moderate, or severe; and inflammation that is symptom or a result of a disease state or syndrome, e.g., hepatitis type B liver inflammation. Inflammation, as used herein, can be characterized at the "whole body" level as several localized manifestations (indices), including hemodynamic disorders (e.g., hyperemia and edema), pain, temperature increment, and functional lesion. All indices may be observed in certain instances, although any particular indication is not necessarily always present. Concomitant cellular and molecular levels changes that characterize inflammation may include leukocyte extravasation (a process involving adhesion of leukocytes to the endothelium of the vessel wall and migration into tissue where they may phagocytose bacteria, viruses, and cell debris) and platelet aggregation (a mechanism whereby the spread of the infection is prevented).

Molecular level changes which characterize inflammation may include activation of at least three plasma defense systems (complement, kinin, and coagulation/fibrinolysis cascades) and synthesis of cytokines and eicosanoids.

Inflammation as described above, refers to both cutaneous inflammation (e.g., skin, muscle or joint derived) and visceral inflammation (e.g., organ derived). Cutaneous inflammation includes but is not limited to arthritis and dermatitis. "Arthritis" as used herein refers to, but is not limited to, for example, rheumatoid arthritis, juvenile arthritis, psoriatic arthritis, Reiter's syndrome, ankylosing spondylitis arthritis, and gouty arthritis. "Dermatitis" as used herein is a disorder caused by inflammation to the skin including endogenous and contact dermatitis such as, but not limited to, actinic dermatitis (or photodermatitis), atopic dermatitis, chemical dermatitis, cosmetic dermatitis, dermatitis aestivalis, and seborrheic dermatitis.

The term "platelet-aggregation" as used herein refers to the process by which platelets bind to each other, e.g., at the site of vascular injury, forming a platelet plug.

The phrase "side effects" encompasses unwanted and adverse effects of a prophylactic or therapeutic agent, e.g., aspirin. Adverse effects are always unwanted, but unwanted effects are not necessarily adverse. An adverse effect from a prophylactic or therapeutic agent might be harmful or uncomfortable or risky. In certain embodiments, side effects from the administration of aspirin, aspirin derivatives, other NSAIDs and anti-inflammatories include those which result from an inhibition of TAFI, such as liver damage, stomach distress and bleeding complications, including but not limited to GI upset, occult bleeding, easy bruising, tinnitus, renal dysfunction and bronchospasm. Side effects from administration of SA include but are not limited to liver damage, stomach distress and bleeding complications, including but not limited to GI upset, occult bleeding, easy bruising, tinnitus, renal dysfunction and bronchospasm.

The term "prophylactic agent" means an agent capable of preventing or reducing the risks or incidence of a disease or disorder in a patient. In certain embodiments the prophylactic agent is capable of preventing or reducing the risks or incidence of thrombosis, hemorrhage, pain, inflammation, platelet aggregation, colon cancer or pancreatic cancer.

The phrase "prophylactically effective amount" refers to that amount of the prophylactic agent sufficient to result in the prevention or reduction in the risk or incidence of a disease or disorder, such as a fever, a hemorrhagic, thrombotic, pain, inflammatory, platelet aggregation disease or disorder, colon cancer or pancreatic cancer. Further, a prophylactically effective amount with respect to a prophylactic agent of the invention means that amount of prophylactic agent alone, or in combination with other agents, that provides a prophylactic benefit in the prevention of the disease or disorder.

The term "therapeutic agent" means an agent capable of modifying, controlling, delaying or reversing a disease or disorder or ameliorating the symptoms of a disease or disorder in a patient. In one embodiment, the therapeutic agent is one which is capable of modifying, controlling, delaying, reversing or ameliorating the symptoms of a fever, a hemorrhagic, thrombotic, pain, inflammatory, platelet aggregation disease or disorder, colon cancer or pancreatic cancer.

The phrase "therapeutically effective amount" refers to that amount of the therapeutic agent sufficient to modify, control, reverse or ameliorate the symptoms of the disease or disorder. In certain embodiments, the disease or disorder is a fever, a hemorrhagic or thrombotic disorder, pain, inflammatory disorder, platelet aggregation disorder, colon cancer or pancreatic cancer. A therapeutically effective amount may refer to the amount of therapeutic agent sufficient to delay, minimize, reverse or ameliorate the symptoms of the disease or disorder. A therapeutically effective amount may also refer to the amount of the therapeutic agent that provides a therapeutic benefit in the treatment or management of the disease disorder. Further, a therapeutically effective amount with respect to a therapeutic agent of the invention means that amount of therapeutic agent alone, or in combination with other therapies, that provides a therapeutic benefit in the treatment or management of the disease or disorder, including the amelioration of symptoms associated with the disease or disorder being treated. A therapeutically effective amount may vary with a patient's age, condition and sex, as well as the extent of the disease in the patient and can be determined by one of skill in the art. The dosage may be adjusted by the individual physician or Veterinarian in the event of any complication.

A therapeutically effective amount typically will vary from about 50-5,000 mg/day in one or more dose administrations daily, for one or several days, depending on the mode of administration and other factors that are apparent to one of skill in the art.

The phrase "a therapeutically effective amount" as used herein in the context of an analgesic refers to an amount of a compound effective to alleviate pain in vivo. The phrase "a therapeutically effective amount" as used herein in the context of a fever reducing compound refers to an amount of a compound effective to reduce the body temperature of a patient who is experiencing a fever. The phrase "a therapeutically effective amount" as used herein in the context of an anti-inflammatory refers to an amount of a compound effective to alleviate inflammation in vivo. The phrase "a therapeutically effective amount" as used herein in the context of an anti-platelet aggregation compound refers to an amount of a compound effective to alleviate platelet aggregation in vivo. The phrase "a therapeutically effective amount" as used herein in the context of a prophylactic colon cancer compound refers to an amount of a compound effective to prevent or reduce a patient's risk of colon cancer in vivo. The phrase "a therapeutically effective amount" as used herein in the context of a prophylactic pancreatic cancer compound refers to an amount of a compound effective to prevent or reduce a patient's risk of pancreatic cancer in vivo. The phrase "a therapeutically effective amount" as used herein in the context of a TAFI inhibitor refers to an amount of a compound effective to promote fibrinolysis in vivo.

The phrase "in combination" refers to the use of more than one prophylactic and/or therapeutic agents against a disease or disorder, e.g., pain disorder and inflammation disorder. In combination may refer to administration that is simultaneous, sequential and/or cyclical. In certain embodiments, agents administered in combination may be administered in the same pharmaceutical composition or separate pharmaceutical compositions.

The term "patient" refers to a mammal such as a non-primate (e.g., cows, pigs, horses, cats, dogs, mice, rats etc.) or a primate (e.g., monkeys and humans). Preferably the patient is a human.

The terms "manage", "managing" and "management" refer to the beneficial effects that a patient derives from a prophylactic or therapeutic agent, which does not result in a cure of the disorder. In certain embodiments, a patient is administered one or more prophylactic or therapeutic agents to "manage" a disease or disorder, or symptoms associated with the disease or disorder, so as to prevent the progression or worsening of the disease or disorder.

The terms "prevent", "preventing" and "prevention" refer to the prevention of the recurrence, spread or onset of a disease or disorder, such as a pain, fever, inflammation, platelet aggregation disease or disorder, colon cancer or pancreatic cancer, or symptoms associated with the disease or disorder, in a patient resulting from the administration of a prophylactic or therapeutic agent.

The terms "treat", "treating" and "treatment" refer to the modification, control, reversal or amelioration of the symptoms of the disease or disorder, such as a pain, fever, inflammation, platelet aggregation disease or disorder, colon cancer or pancreatic cancer that results from the administration of one or more prophylactic or therapeutic agents. In certain embodiments, such terms refer to the minimizing or delay of the hemorrhagic or thrombotic disease or disorder resulting from the administration of one or more prophylactic or therapeutic agents to a patient with such a disease or disorder. In other embodiments, such terms refer to the amelioration of one or more symptoms associated with an inflammatory disorder that results from the administration of one or more prophylactic or therapeutic agents. In certain embodiments, such terms refer to a reduction in the swelling of one or more joints, or a reduction in the pain associated with an inflammatory disorder resulting from the administration of one or more prophylactic or therapeutic agents to a patient with such a disorder. In other embodiments, such terms refer to a reduction in a patient of the symptoms of a fever, pain, platelet aggregation, colon cancer or pancreatic cancer that results from the administration of one or more prophylactic or therapeutic agents.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, i.e., they allow for elements not explicitly recited, but exclude elements that are found in the prior art or that affect a basic or novel characteristic of the invention. The singular forms "a", "an" and "the" include plural referents, unless the content clearly dictates otherwise. Thus, for example, reference to "an antigen" includes a mixture of two or more antigens, reference to "an excipient" includes mixtures of two, or more excipients, etc.

Methods of Screening Compounds

In one embodiment, this invention provides assays for screening test compounds for TAFIa inhibitory or non-inhibitory activity and for the ability to treat, prevent or manage pain, fever, inflammation, platelet aggregation, colon cancer, pancreatic cancer, thrombotic and fibrinolytic diseases and disorders, i.e., for other aspirin activities.

Test Compounds

The test compounds of the present invention can be obtained using any of the numerous approaches in combinatorial library methods known in the art, including but not limited to biological libraries, spatially addressable parallel solid phase or solution phase libraries, synthetic library methods requiring deconvolution, the "one-bead one-compound" library method, and synthetic library methods using affinity chromatography selection. The biological library approach is used with peptide libraries, while the other four approaches are applicable to peptide, non-peptide oligomer or small molecule libraries of compounds (Lam, K. S. (1997) *Anticancer Drug Des.* 12:145.

Examples of methods for the synthesis of molecular libraries can be found in the art, for example, in: DeWitt et al.

(1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In particular, any known analgesic, antipyretic, anti-inflammatory, anti-platelet aggregation, colon cancer prophylactic, pancreatic cancer prophylactic, fibrinolytic or thrombotic agent may be screened by the methods of the invention including but not limited to aspirin, ibuprofen, acetominophen, Nabumetone (RELAFEN®), salsalate, Etodac (LODINE®), Ibuprofen, Aspirin, Diclofenac (VOLTAREN®, CATAFLAM®), Sulindac (CLINORIL®), Diflunisal (DOLOBID®), Naproxen (NAPROSYN®, ALLEVE®), Indomethacin (INDOCIN®), Tolmetin sodium (TOLECTIN®), Fenoprofen calcium (NALFON PULVULES®), Ketoprofen (ORUDIS®, ORUVAIL®), Piroxicam (FELDENE®), Flubiprofen (ANSAID®), Meclofenamate sodium (MECLOMEN®), Ketorolac tromethamine (TORADOL®), Oxaprozin (DAYPRO®), COX-1 inhibitors, and COX-2 inhibitors including but not limited to CELEBREX® and Vioxx®, and metabolites and derivatives thereof.

Compounds identified by the methods of the invention may then be derivatized using methods well known to one of skill in the art. Additionally, compounds may be designed through rational drug design procedures known in the art. In a particular embodiment, compounds which mimic the TAFIa inhibitory activity of salicylic acid, salicyluric acid or gentisic acid may be designed through rational drug design procedures. These procedures include, but are not limited to X-ray crystallography, computer assisted modeling and analog synthesis.

In another embodiment, antibodies are screened by the methods of the invention. In particular, antibodies may be screened for analgesic, antipyretic, anti-inflammatory, anti-platelet aggregation, colon cancer prophylactic and/or colon cancer prophylactic activities.

In one embodiment, monoclonal antibodies can be screened. In another embodiment, libraries of antibodies can be screened. In particular, phage display methods may be utilized wherein functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen (e.g., a polypeptide) can be selected or identified with antigen (e.g., TAFI), e.g., using labeled antigen or antigen bound or captured to a solid surface or bead. Alternatively, phage can be assayed in the assay methods of the invention. Examples of phage display methods that can be used to make the antibodies of the present invention include those disclosed in Brinkman et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, *Gene* 187:9-18; Burton et al., 1994, *Advances in Immunology* 57:191-280; PCT Application No. PCT/GB91/O1 134; PCT Publication Nos. WO 90/02809, WO 91/10737, WO 92/01047, WO 92/18619, WO 93/1 1236, WO 95/15 982, WO 95/20401, and WO97/13844; and U.S. Pat. Nos. 5,698, 426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including subjectian cells, insect cells, plant cells, yeast, and bacteria, e.g., as described below. Techniques to recombinantly produce Fab, Fab' and F(ab')2 fragments can also be employed using methods known in the art such as those disclosed in PCT Publication No. WO 92/22324; Mullinax et al., 1992, *BioTechniques* 12(6):864-869; Sawai et al., 1995, *AJRI* 34:26-34; and Better et al., 1988, *Science* 240:1041-1043.

Methods of Screening for Compounds to Treat, Prevent or Manage Pain, Fever, Inflammation, Platelet-Aggregation, Colon Cancer or Pancreatic Cancer One aspect of the invention provides a method of screening for compounds which retain at least one aspirin activity, e.g. COX-2 activity, but do not inhibit TAFIa activity and/or TAFI activation. In preferred embodiments, the test compounds are screened for at least one other aspirin activity such as ability to treat, prevent or manage pain, fever, inflammation, platelet aggregation, colon cancer, pancreatic cancer, COX-1 and/or COX-2 inhibition.

In one embodiment, the invention provides a method of screening compounds for at least one aspirin activity including, but not limited to, analgesia, fever reduction, anti-inflammation, anti-platelet aggregation, colon cancer prophylaxis and pancreatic cancer prophylaxis, and for non-inhibition of TAFI. The method comprises the steps of (a) exposing TAFI to a test compound, (b) determining whether the test compound modulates TAFIa activity and/or TAFI activation and (c) determining whether at least one aspirin activity is retained by the test compound. In a particular embodiment, a method of screening for analgesic activity and non-inhibition of TAFI is provided. In a particular embodiment, a method of screening for antipyretic activity and non-inhibition of TAFI is provided. In another embodiment, a method of screening for anti-inflammatory activity and non-inhibition of TAFI is provided. In another embodiment, a method of screening for anti-platelet aggregation and non-inhibition of TAFI is provided. In another embodiment, a method of screening for colon cancer prophylaxis and non-inhibition of TAFI is provided. In a particular embodiment, a method of screening for pancreatic cancer prophylaxis and non-inhibition of TAFI is provided.

A second aspect of this invention relates to screening compounds for TAFIa inhibitory activity, comprising (a) exposing TAFI to a test compound; and (b) determining whether the test compound inhibits TAFIa activity and/or TAFI activation. In a particular embodiment, the method further comprises comparing the TAFI inhibitory activity of the test compound to that of a compound selected from the group consisting of acetylsalicylic acid, salicylic acid, salicyluric acid or gentisic acid. In a particular embodiment, the invention relates to a method of screening compounds for anti-TAFIa/TAFI activity but not aspirin activity.

The analgesic, antipyretic, anti-inflammatory, anti-platelet aggregation, colon cancer prophylactic or pancreatic cancer prophylactic activity of a test compound can be assessed using a variety of in vitro and in vivo assays known to one of skill in the art.

COX-1 and COX-2 activity may be measured by various methods well known in the art. In particular, COX-1 activity may be assessed by determining platelet aggregation and thromboxane (TX) production. COX-2 activity may be measured by assessing prostaglandin 2 (PGE2) production in lipopolysaccharide (LPS)-stimulated monocytes. In preferred embodiments, the in vitro studies are conducted by taking whole blood from healthy patients and exposing it to the test compound. In preferred embodiments, ex vivo studies are conducted using whole blood from patients exposed to drugs. In a particularly preferred embodiment, the ex vivo whole blood assay methods described in Patrignani et al., 1994, *J. Pharmacol. Exp. Ther.* 271:1705-1712 are used. Other preferred assays for determining COX-1 and COX-2 inhibition include but are not limited to those described in Vane et al., 1998, *Am. J. Med.*, 104:2 S-8S; Fenner, H., 1997, *Semin. Arthritis Rheum.* 26:28-33; Cryer, B. and Feldman, M., *Am. J. Med.* 104:413-421.

The analgesic activity of a compound of the invention may be evaluated, for example, in vivo by the formalin test. In the formalin test, mice are administered an IP dose of the test compound or a control (i.e., a known analgesic or a non-analgesic) compound. Thirty minutes later, a formalin solution is injected into the plantar surface of the right hind paw. For thirty minutes immediately following the injection, the mice are observed and the time spent licking the paw (a response to pain) is measured using a timer. The time spent licking the right hind paw by a control mouse is compared to that spent licking by a mouse that was administered the test compound.

Additionally, the analgesic effect of a compound may be evaluated in vivo by the hotplate test. In the hotplate test, mice are administered a dose of the test compound or control compound. One hour later, the mice are placed on a metal surface heated to 55° C. When the mouse licks its hind paw or after 30 seconds, it is removed from the surface, and the latency to the lick is measured. The time difference between the treated and control mice is then compared.

In one embodiment of the invention, pain is alleviated by at least 400%, at least 350-400%, at least 300-350%, at least 275-300%, at least 250-275%, at least 225-250%, at least 200-225%, at least 150-200%, at least 100-150%, at least 50-100% or at least 1-50% as compared to equivalent amounts of a known analgesic. Known analgesics include but are not limited to aspirin, VIOXX®, CELEBREX®, ibuprofen, acetaminophen, codeine and other NSAIDs. In preferred embodiments, pain is alleviated by more than 200%, as compared to equivalent amounts of a known analgesic.

The anti-inflammatory activity of therapies used in accordance with the present invention can be determined by using various experimental animal models of inflammatory arthritis known in the art and described in Crofford L. J. and Wilder, R. L., "Arthritis and Autoimmunity in Animals", in Arthritis and Allied Conditions: A Textbook of Rheumatology, McCarty et al., (eds.), Chapter 30 (Lee and Febiger, 1993). The following assays are provided as examples and not by limitation.

The principle animal models for arthritis or inflammatory disease known in the art and widely used include: adjuvant-induced arthritis rat, rabbit and hamster models, all described in Crofford L. J. and Wilder, R. L., "Arthritis and Autoimmunity in Animals". In Arthritis and Allied Conditions: A Textbook of Rheumatology, McCarty et al., (eds.), Chapter 30 (Lee and Febiger, 1993).

The anti-inflammatory activity of the therapy may be determined using a carrageenan-induced arthritis rat model. Carrageenan-induced arthritis has previously been used in rabbit, dog and pig studies of chronic arthritis or inflammation. Quantitative histomorphometric assessment is used to determine therapeutic efficacy. The methods of using such carrageenan-induced arthritis model are described in Hansra P., et al., 2000, *Inflammation* 24(2):141-155.

Additionally, the anti-inflammatory activity of a test compound may be evaluated by the pleural exudation assay, the formaldehyde induced arthritis assay or the cotton pellet implantation assay as fully described in Spector, W. G., 1956, *J. Path. Bact.* 12:367-380, Brownlee, G., 1950, *Lancet* 1: 157-159, and Meier, R., Schuler W., and Desaulles, P., 1950, *Experintia* 6:469, respectively. Briefly, experimental pleurisy is produced by injecting a rat with 0.1 mL of turpentine into the right pleural space under light ether anaesthesia. The test anti-inflammatory compound may be injected intraperitoneally in graded doses 1 hour before turpentine injection. The rats are decapitated and pleural exudate is collected half and hour after turpentine treatment. The volume of exudate is measured and compared to that of rats that have been administered control substances or known anti-inflammatories.

In the formaldehyde induced arthritis assay, 0.1 mL of 2% (v/v) formaldehyde is injected subcutaneously under the plantar aponeurosis in each foot of the rat on the first and third days. The test anti-inflammatory compound may be given intraperitoneally once daily for 10 days in graded doses. Day-to-day changes in the inflammatory reaction are assessed by measuring the linear cross-section immediately below the ankle joint with a micrometer screw gauge. The diameter of ankle is then compared to that of rats that have been administered control substances or known anti-inflammatories.

In the cotton implantation assay, pellets of surgical cotton weighing 9.0±1 mg are sterilized in an air oven for 2 hours and implanted in both the axillae and groins under ether anaesthesia. The test anti-inflammatory compound is given intraperitoneally in graded doses daily for 6 days. The pellets are dissected out on the $7^{th}$ day under light ether anaesthesia. They are kept separately in small glass vials, dried for 2 hours at temperature of 150 C. and weighed after cooling. The weight of granulation tissue is then compared to that of rats that have been administered control substances or known anti-inflammatories.

The anti-inflammatory cyclo-oxygenase inhibitory activity of a test compound may be screened by the ovine ureteral motility assay as described in Bhargava, K. P. and Thulesius, O., 1987, *Gen. Pharmacol.* 18(3):337-40. Briefly, an isolated sheep ureteral ring is suspended in an organ bath. The ureteral ring will exhibit rhythmic contractions which are dose-dependently inhibited by indomethacin and revived by prostaglandin E2 or F2 alpha. Test compounds are tested on the isolated ureteral ring model to determine the time elapsing from application of test compound to complete inhibition of ureteral contraction, i.e., "stop time." Stop times are then compared to stop times in the absence of the compound or in presence of a control substance or a known cyclo-oxygenase inhibitor.

The invention also provides methods of screening anti-platelet aggregation in vivo and in a patient. For example, platelet aggregation may be evaluated using the procedure described in Aguejouf et al 2000, *Thrombosis Research* 99: 595-602. In brief, a rat is exposed to a test compound, administered anesthesia and then a median laparotomy is performed. The intestinal loop is placed on a microscope table and vascular lesions are induced by a laser (e.g. Stabilite 2016, Spectra Physics, France). The procedure lasts 10 minutes and is repeated for each rat. Platelet aggregation is then evaluated according to the methods described in Cardinal, D. and Flower, R., 1980, *J. Pharmacological Methods* 135-8.

In one embodiment of the invention, platelet aggregation is reduced by at least 91-100%, 81-90%, 71-80%, 61-70%, 51-60%, 41-50%, 31-40%, 21-30%, 11-20% or 1-10% as compared to equivalent amounts of a known anti-platelet aggregation compound, including but not limited to aspirin. In preferred embodiments, platelet aggregation is reduced by more than 100% as compared to equivalent amounts of a known anti-platelet aggregation compound.

Test compounds which retain the desired amount of at least one aspirin activity can then be tested for modulation of TAFIa activity. In a preferred embodiment, the test compounds are tested for non-inhibition of TAFIa activity. In a particular embodiment, test compounds are screened for modulation of TAFIa carboxypeptidase activity. In a preferred embodiment, test compounds are screened for the ability to block, inhibit or retard the cleavage of fibrin or other substrates by TAFIa. In one embodiment, TAFIa carboxypeptidase activity is measured using a fluorometric in vitro assay. In particularly preferred embodiments, TAFIa carboxypeptidase activity may be measured according to the exemplary teachings set forth in U.S. patent application Ser. No. 10/116,095, filed Apr. 4, 2002 and U.S. Provisional Patent Application No. 60/406,756 entitled "Diagnostic Assay for Thrombin-Activatable Fibrinolysis Inhibitor (TAFI)", by Greenfield and An. In a particularly preferred embodiment, levels of TAFIa may be measured using the ELISA procedure described therein. In certain embodiments, modulation of TAFIa activity may be measured by determining whether TAFIa enzymatic activity is changed in step (a) relative to TAFIa exposed to aspirin, salicylic acid, salicyluric acid or gentisic acid.

TAFIa activity may by measured by the clot lysis assay. See Reed, G., et al., 1990, *Proc. Nat'l Acad. of Sci. USA* 87: 1114-1118 as described in U.S. Pat. No. 6,114,506, issued Sep. 5, 2000.

TAFIa activity may also be measured by the fibrinogen assay. See Rampling, M. W. and Gaffney, P. J., 1976, *Clin. Chim, Acta.* 67: 43-53, which is hereby incorporated be reference in its entirety. See U.S. Pat. No. 6,114,506, issued Sep. 5, 2000.

In a preferred embodiment, TAFIa is preincubated with the test compound for about 1 hour. In various embodiments, TAFIa is preincubated with the test compound for about 30 minutes, less than 30 minutes, at least 30 minutes, less than 1 hour, at least 1 hour, about 2-3 hours, about 4-5 hours, about 6-8 hours, about 8-10 hours, about 10-12 hours, about 12-16 hours, about 16-20 hours, about 24 hours, at least 24 hours or less than 24 hours. In one embodiment, TAFIa is preincubated with the test compound at around room temperature. In another embodiment, TAFIa is preincubated with the test compound at around 37° C.

In another embodiment, modulation of TAFIa activity is measured by determining whether TAFI proenzyme to TAFIa conversion is changed in step (a) relative to TAFIa exposed to aspirin, salicylic acid, salicyluric acid or gentisic acid. In a particular embodiment, TAFI proenzyme to TAFIa conversion by thrombin/thrombomodulin in the presence of a test compound is measured. The levels of TAFI proenzyme can be compared to levels of TAFIa in aspirin and aspirin metabolite exposed samples. In a preferred embodiment, TAFIa is preincubated with the test compound for about 1 hour.

In preferred embodiments, the test compound inhibits TAFI activity and/or activation by at least 100%, about 100%, about 50-100%, about 25-50%, about 1-25%, preferably about 1-15%, or most preferably about 1-5%, as compared to aspirin, salicylic acid, salicyluric acid or gentisic acid. Alternatively, the test compound promotes TAFI activity and/or activation.

Methods of Screening for Compounds to Treat, Prevent or Manage Fibrinolysis or Thrombosis The instant invention provides methods of screening compounds for TAFIa inhibitors. Such compounds are useful for the treatment of thrombotic diseases including but not limited to angina pectoris, chronic stable angina pectoris, heart attack, stroke, thromboembolic disease, myocaridal infarction (MI), acute myocardial infarction (AMI), recurrent myocardial infarction, ischemic attack, transient ischemic attack (TIA), deep vein thrombosis, acute ischemic stroke, massive pulmonary embolism, disseminated intravascular coagulation (DIC), anti-phospholipid syndrome, familial thrombophilia, sepsis, arthritis, fulminant hepatitis, thrombosis, hemophilia and Von Willebrand disease.

In one embodiment, modulation of TAFIa activity is measured by determining whether TAFIa enzymatic activity is changed in step (a) relative to TAFIa exposed to aspirin, salicylic acid, salicyluric acid or gentisic acid. In a particular embodiment, test compounds are screened for those which block, inhibit or retard the cleavage of fibrin or other substrates by TAFIa. In a particular embodiment, inhibition of TAFIa carboxypeptidase activity is measured. In a preferred embodiment, TAFIa carboxypeptidase activity is measured using a fluorometric in vitro assay. In particularly preferred embodiments, TAFIa carboxypeptidase activity may be measured according to the exemplary teachings set forth in U.S. patent application Ser. No. 10/116,095, filed Apr. 4, 2002 and U.S. Provisional Patent Application No. 60/406,756, entitled "Diagnostic Assay for Thrombin-Activatable Fibrinolysis Inhibitor (TAFI)", by Greenfield and An. In a particularly preferred embodiment, levels of TAFIa may be measured using the ELISA procedure described therein.

In a preferred embodiment, TAFIa is preincubated with the test compound for about 1 hour. In various embodiments, TAFIa is preincubated with the test-compound for less than 1 hour, at least 1 hour, about 30 minutes; about 2-3 hours, about 4-5 hours, about 6-8 hours, about 8-10 hours, about 10-12 hours, about 12-16 hours, about 16-20 hours, about 24 hours, at least 24 hours or less than 24 hours. In one embodiment, TAFIa is preincubated with the test compound at room temperature. In another embodiment, TAFIa is preincubated with the test compound at 37° C.

In another embodiment, modulation of TAFIa activity is measured by determining whether TAFI proenzyme to TAFIa conversion is changed in step (a) relative to TAFIa exposed to aspirin, salicylic acid, salicyluric acid or gentisic acid. In a particular embodiment, TAFI proenzyme to TAFIa conversion by thrombin/thrombomodulin in the presence of a test compound is measured. The levels of TAFI proenzyme can be compared to levels of TAFIa in aspirin and aspirin metabolite exposed samples. In a preferred embodiment, TAFIa is preincubated with the test compound for about 1 hour. In another embodiment, TAFIa is preincubated with the test compound for about 30 minutes.

In certain embodiments, the test compound reduces TAFIa activity by at least at least 400%, at least 375-400%, at least 350-375%, at least 325-350%, at least 300-325%, at least 275-300%, at least 250-275%, at least 225-250%, at least 200-225%, at least 150-200% at least 100-150%, at least 50-100% or at least 1-50% as compared to TAFIa activity in the absence of the test compound. In certain embodiments, the modulation of TAFIa activity in the presence of the test compound is compared to TAFIa activity in the presence of equivalent amounts of known TAFIa inhibitors such as aspirin, salicylic acid, salicyluric acid or gentisic acid.

Pharmaceutical Formulations and Applications

The compounds identified by the methods of the invention are useful in the methods of treatment, prevention and management of pain, fever, inflammation, platelet aggregation, fibrinolysis, thrombosis, colon cancer, pancreatic cancer and the diseases and disorders associated therewith. Additionally, the compounds identified by the screening methods of the present invention can used in prophylactic and therapeutic methods, administered to the patient population, used in combination therapy, formulated in pharmaceutical compositions, and administered by the methods and in the dosages set forth in the following sections of the specification.

Prophylactic and Therapeutic Methods Using the Compounds of the Invention

The present invention encompasses methods for treating, preventing, or managing any disease or disorder which can be treated, prevented or managed by aspirin therapy, other NSAIDs or anti inflammatories. The present invention also encompasses methods of eliminating at least one aspirin associated adverse side effect that can be prevented or managed by modulating TAFIa activity.

Hemorrhagic and thrombotic diseases and side effects occur, in part, because the normal balance between the coagulation and fibrinolytic cascades has been affected, altered or shifted. The methods of the present invention allow the balance of the cascades to be shifted by individually increasing or decreasing one of the respective cascades without affecting the other, e.g., by providing TAFIa activity to compensate for the TAFIa inhibitory activity of aspirin.

Another aspect of the present invention is directed to a method of treating, preventing or managing bleeding side-effects associated with the administration of aspirin or any other anti-coagulant, such as tissue plasminogen activator (t-PA), urokinase plasminogen activator (u-PA), streptokinase, staphylokinase, plasminogen or analogs thereof, heparin or low molecular weight heparin, or an anti-inflammatory, such as hydrocoftisone, sodium salicylate, oxyphenbutazone, indomethacin or cyproheptadine, or any other anti-cancer drug, such as methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel, doxorubicin, epirubicin, 5-fluorouracil, taxanes such as docetaxel and paclitaxel, leucovorin, levamisole, irinotecan, estramustine, etoposide, nitrosoureas such as carmustine and lomustine, vinca alkaloids, platinum compounds, mitomycin, gemcitabine, hexamethylmelamine and topotecan, comprising administering a therapeutically or prophylactically effective amount of a compound which maintains other aspirin activities, e.g., COX-2 activity, but does not inhibit TAFIa activity or TAFI activation. In one embodiment, the aspirin activity is analgesia. In another embodiment, the aspirin activity is anti-pyretic activity. In another embodiment, the aspirin activity is anti-inflammation activity. In another embodiment, the aspirin activity is anti-platelet aggregation activity. In another embodiment, the aspirin activity is colon cancer prophylaxis. In another embodiment, the aspirin activity is pancreatic cancer prophylaxis.

Another aspect of the present invention is directed to a method of treating, preventing or managing bleeding side-effects associated with the administration of aspirin or any other anti-coagulant, such as, tissue plasminogen activator (t-PA), urokinase plasminogen activator (u-PA), streptokinase, staphylokinase, plasminogen or analogs thereof, heparin or low molecular weight heparin, or an anti-inflammatory, such as hydrocortisone, sodium salicylate, oxyphenbutazone, indomethacin or cyproheptadine, or an anti-cancer drug, such as methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel, doxorubicin, epirubicin, 5-fluorouracil, taxanes such as docetaxel and paclitaxel, leucovorin, levamisole, irinotecan, estramustine, etoposide, nitrosoureas such as carmustine and lomustine, vinca alkaloids, platinum compounds, mitomycin, gemcitabine, hexamethylmelamine and topotecan, comprising administering a therapeutically or prophylactically effective amount of stabilized TAFIa. In a particular embodiment, stabilized TAFIa is administered prior to the administration of aspirin or other therapeutic agent. In another particular embodiment, stabilized TAFIa is administered subsequent to the administration of aspirin or other therapeutic agent. In another embodiment, stabilized TAFIa is administered concurrently with aspirin or other therapeutic agent. In another embodiment, stabilized TAFIa is administered simultaneously, e.g., in the same composition, as the administration of aspirin or other therapeutic agent.

The term "concurrently" is not limited to the administration of prophylactic or therapeutic agents at exactly the same time, but rather it is meant that the agents are administered within a time interval such that the two agents can work together. For example, one agent may be administered one time per week in combination with another agent that is one time every two weeks or one time every three weeks.

The therapeutic or prophylactic: agents used in combination may be administered by the same or different routes of administration, e.g., oral and parenteral.

In certain embodiments, the prophylactic or therapeutic agents of the invention are cyclically administered in combination to a patient. Cycling therapy involves the administration of a first agent for a period of time, followed by administration of a second agent and/or third agent for a period of time and repeating this sequential administration. Cycling therapy reduces the development of resistance to one or more of the therapies, avoids or reduces the side effects of one of the therapies, and/or improves the efficacy of the treatment.

Another aspect of the present invention is directed to a method of treating, preventing or managing a thrombotic disease or disorder comprising administering a therapeutically or prophylactically effective amount of a compound of the invention, e.g., as identified by the screening methods of the invention, or a pharmaceutical composition thereof, to a patient. In certain embodiments, the thrombotic diseases or disorders include, but are not limited to, heart attack, stroke, thromboembolic disease, acute myocardial infarction (AMI), deep vein thrombosis, acute ischemic stroke, massive pulmonary embolism, disseminated intravascular coagulation (DIC), familial thrombophilia, sepsis, arthritis, fulminant hepatitis and thrombosis. In preferred embodiments, the inhibitor of TAFIa is salicylic acid.

Suitable regimens can be selected by one skilled in the art by considering such factors and by following, for example, dosages reported in the literature and recommended in the *Physician's Desk Reference* (56*th* ed., 2002).

Patient Population

The invention provides methods of treating a patient suffering from pain, fever, colon cancer, pancreatic cancer, coronary artery disease, inflammatory disease, platelet aggregation disease or fibrinolytic disease which can be treated, prevented or managed by administering to the patient a therapeutically or prophylactically effective amount of a compound identified by the screening methods of the present invention, or a pharmaceutical composition thereof.

The invention also provides methods of treating a patient suffering from a thrombotic or hemorrhagic disorder, or any other disease or disorder associated with aberrant levels of TAFIa or which can be treated, prevented or managed by decreasing TAFIa activity, by administrating to a patient a therapeutically or prophylactically effective amount of an inhibitor of TAFIa identified by a screening method of the invention, or pharmaceutical composition thereof.

The patient is preferably a mammal such as a non-primate (e.g., cows, pigs, horses, cats, dogs, mice, rats etc.) or a primate (e.g., monkeys, such as cynomolgus monkeys, and humans). In a preferred embodiment, the patient is a human.

The invention also encompasses methods for treating patients that are receiving or have received any other treatment useful for the prevention of pain, fever, inflammation, platelet aggregation, colon cancer, pancreatic-cancer, thrombotic or hemorrhagic diseases or disorders. In another embodiment, the patient has never received any other treatment useful for the prevention of pain, fever, inflammation, platelet aggregation, colon cancer, pancreatic cancer, thrombotic or hemorrhagic diseases or disorders.

Patients can be treated for somatic pain, neuropathic pain, localized inflammation, systemic inflammation, arthritis or dermatitis using the methods of the invention.

Using the methods of the present invention, patients can be treated for the prevention, treatment or management of hemorrhagic or thrombotic diseases or disorders, including, but not limited to, heart attack, stroke, thromboembolic disease, hemophilia, von Willebrand disease (VWD), acute myocardial infarction (AMI), deep vein, thrombosis, acute ischemic stroke, massive pulmonary embolism, disseminated intravascular coagulation (DIC), familial thrombophilia, sepsis, arthritis, Fulminant hepatitis, Henoch-Schonlein purpura, hemostasis and thrombosis, or any disease or disorder characterized by excessive clotting. In one embodiment, patients can be treated for hemorrhagic diseases or disorders which include, but are not limited to, hemophilia A, hemophilia B, autoimmune haemolytic anaemia, collagen diseases, von Willebrand disease (VWD), Henoch-Schonlein purpura, acute-generalized widespread bleeding, primary hyperfibrinolysis, hepatosplenic schistosomiasis, factor deficiencies and hemostasis.

In another embodiment, the methods of the present invention are useful for the amelioration of symptoms associated with hemorrhagic or thrombotic diseases or disorders. The methods and compositions of the invention can be used with one or more conventional or experimental therapies that are used to prevent, treat or manage hemorrhagic or thrombotic diseases or disorders.

In one embodiment, the invention provides methods for treating, preventing, or managing thrombotic diseases or disorders by administrating a therapeutically or prophylactically effective amount of a TAFIa inhibitor identified by a method of the invention, or a pharmaceutical composition thereof to a patient currently undergoing alternative treatment for a thrombotic disease or disorder.

In another embodiment, the invention provides methods for treating, preventing, or managing thrombotic diseases or disorders by administrating a therapeutically or prophylactically effective amount of a TAFIa inhibitor identified by a method of the invention, or a pharmaceutical composition thereof to a patient who has previously undergone treatment for a thrombotic disease or disorder.

In another embodiment, the invention provides methods for treating, preventing, or managing thrombotic diseases or disorders by administrating a therapeutically or prophylactically effective amount of a TAFIa inhibitor identified by a method of the invention, or a pharmaceutical composition thereof to a patient who has never undergone treatment for a thrombotic disease or disorder.

Combination Therapies

According to the invention, therapy by administration of a compound of the invention, or a pharmaceutical composition thereof is combined with the administration of one or more therapeutic or prophylactic agents such as, but not limited to, analgesics, antipyretics, anti-inflammatories, anti-platelet aggregation compounds, colon cancer prophylactics, pancreatic cancer prophylactics and procoagulant agents. When used in combination with other prophylactic and/or therapeutic agents, the compounds identified by the screening methods of the present invention, or pharmaceutical compositions thereof, can be administered prior to, subsequent to or concurrently with the other therapeutic or prophylactic agents.

In one embodiment, the therapeutic or prophylactic agent is useful for the treatment, prevention or management of at least one of the following: pain, fever, inflammation, platelet aggregation, fibrinolysis or hemorrhage, colon cancer or pancreatic cancer. In other embodiments, the therapeutic or prophylactic agent is useful for the treatment, prevention or management of at least 2-3 of the following: pain, fever, inflammation, platelet aggregation, fibrinolysis or hemorrhage, colon cancer or pancreatic cancer. In other embodiments, the therapeutic or prophylactic agent is useful for the treatment, prevention or management of at least 4-5 of the following: pain, fever, inflammation, platelet aggregation, fibrinolysis or hemorrhage, colon cancer or pancreatic cancer.

In another embodiment, the inhibitor of TAFIa, or pharmaceutical composition thereof, can be administered in combination with another prophylactic or therapeutic agent. When used in combination with other prophylactic and/or therapeutic agents, the inhibitor of TAFIa, or pharmaceutical composition thereof can be administered prior to, subsequent to or concurrently with one or more other therapeutic or prophylactic agents. In one embodiment, the inhibitor of TAFIa, or pharmaceutical composition thereof is administered concurrently with one or more therapeutic or prophylactic agents, e.g., in the same pharmaceutical composition. In another embodiment, the inhibitor of TAFIa, or pharmaceutical composition thereof is administered concurrently with one or more other therapeutic or prophylactic agents in separate pharmaceutical compositions. In certain embodiments, the other therapeutic or prophylactic agent is useful for the treatment, prevention or management of a thrombotic disorder. In other embodiments, the therapeutic or prophylactic agent is not useful for the treatment, prevention or management of a thrombotic disorder. In certain embodiments, the therapeutic or prophylactic agent includes, but is not limited to aspirin, t-PA, heparin, Factor VII, Factor VIII, Factor IX, amino caproic acid, activated protein C, thrombin, fibrinogen, cryofractionalized plasma, actothrombin, low molecular weight heparin, hirudin, plasminogen, streptokinase, staphylokinase, urokinase or hirulong.

Examples of analgesics and anti-inflammatories include but are not limited to aspirin, ibuprofen; acetominophen, methotrexate, Nabumetone (RELAFEN®), salsalate, Etodac (LODINE®), Ibuprofen, Aspirin, Diclofenac (VOLTAREN®), CATAFLAM®), Sulindac (CLINORIL®), Diflunisal (DOLOBID®), Naproxen (NAPROSYN®, ALLEVE®), Indomethacin (INDOCIN®), Tolmetin sodium (TOLECTIN®), Fenoprofen calcium (NALFON PULVULES®), Ketoprofen (ORUDIS®, ORUVAIL®), Piroxicam (FELEDENE®), Flubiprofen (ANSAID®), Meclofenamate sodium (MECLOMEN®), Ketorolac tromethamine (TORADOL®), Oxaprozin (DAYPRO®), COX-1 inhibitors, and COX-2 inhibitors including but not limited to CELEBREX® and VIOXX®. Additional anti-inflammatories include but are not limited to beta-agonists, anticholinergic agents, methyl xanthines and corticosteroids (e.g., prednisone and hydrocortisone).

Examples of anti-coagulant agents include, but are not limited to, t-PA (or analogs thereof), heparin, low molecular weight heparin, aspirin, actothrombin, hirudin, plasminogen, streptokinase, staphylokinase, urokinase or hirulong.

Examples of anti-cancer drugs include, but are not limited to methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel, doxorubicin, epirubicin, 5-fluorouracil, taxanes such as docetaxel and paclitaxel, leucovorin, levamisole, irinotecan, estrarnustine, etoposide, nitrosoureas such as carmustine and lomustine, vinca alkaloids, platinum compounds, mitomycin, gemcitabine, hexamethylmelamine and topotecan.

In one embodiment, a compound of the invention, or a pharmaceutical composition thereof is administered in combination with surgery. The administration can be either prior to surgery, after surgery or concomitant with surgery. Examples of such surgeries include, but are not limited to organ transplant surgery, cardiopulmonary bypass surgery, coronary angioplasty, open heart surgery, heart valve surgery or removal of atherosclerotic plaques. In preferred embodiments, the inhibitor of TAFIa is salicylic acid.

Pharmaceutical Compositions

Pharmaceutical compositions of the present invention comprise a prophylactically or therapeutically effective amount of a compound of the invention, alone or in combination with another prophylactic or therapeutic agent, and a pharmaceutically acceptable carrier. Preferably, compositions of the invention comprise a prophylactically or therapeutically effective amount of a compound of the invention, and a pharmaceutically acceptable carrier.

The term "carrier" refers to a diluent, adjuvant, excipient, or vehicle with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin.

In a preferred embodiment, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as Lidocaine (lignocaine) to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharin, cellulose, magnesium carbonate, etc. Such vehicles are preferably of pharmaceutical grade.

Further, the effect of the compounds of this invention may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

Routes of Administration

Methods of administering a compound of the invention, or a pharmaceutical composition thereof include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, a compound of the invention, or a pharmaceutical composition thereof is administered intramuscularly, intravenously, or subcutaneously. The compound of the invention, or a pharmaceutical composition thereof may also be administered by infusion or bolus injection and may be administered together with other therapeutic or prophylactic agents. Administration can be local or systemic. The compound of the invention, or pharmaceutical composition thereof may also be administered by inhalation or insufflation (either through the mouth or the nose). In a preferred embodiment, local or systemic parenteral administration is used.

In specific embodiments, it may be desirable to administer the compound of the invention, or a pharmaceutical composition thereof, locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound of the invention, or a pharmaceutical composition thereof can be formulated as a suppository, with traditional binders and vehicles such as triglycerides.

In another embodiment, the compound of the invention, or a pharmaceutical composition thereof, can be delivered in a vesicle, in particular a liposome (see Langer, 1990, *Science* 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compound of the invention, or a pharmaceutical composition thereof, can be delivered in a controlled release system. In one embodiment, a pump may be used (see Langer, supra; Sefton, 1987, *CRC Crit. Ref.* *Biomed. Eng.* 14:201; Buchwald et al., 1980, *Surgery* 88:507 Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); *Ranger and Peppas*, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). Other controlled-release systems discussed in the review by Langer, 1990, *Science* 249:1527-1533) may be used.

Dosages

The amount of the compound of the invention, or pharmaceutical composition thereof which will be effective in the treatment, prevention or management of a pain, fever, inflammation, platelet-aggregation, colon cancer, pancreatic cancer, thrombotic or hemorrhagic disease or disorder or other disease or disorder that can be treated, prevented or managed by administration of a compound of the invention can be determined by standard research techniques. For example, the dosage that will be effective in the treatment, prevention or management of a hemorrhagic or thrombotic disease or disorder can be determined by administering the compound of the invention, or pharmaceutical composition thereof to an animal model such as, e.g., the animal models disclosed herein or known to those skilled in the art. In addition, in vitro assays may optionally be employed to help identify optimal dosage ranges. Selection of the preferred effective dose can be determined via clinical trials.

The precise dose to be employed will also depend on the route of administration, and the seriousness of the disease or disorder, and should be decided according to the judgment of the practitioner and each patient's circumstances. Effective doses may be extrapolated from dose-response curves derived from in vitro or animal model test systems.

Animal models include but are not limited to those disclosed in Reyers, I., et al., 1985, *Thromb. Haemost.* 54(3): 619-621; Louie, S, and Gurewich, V., 1983, *Thromb. Res.* 30(4):323-35; Hahn D., et al., 1982, *Prostaglandins* 23(1):1-16; Koster J., et al., 1981, *Artery* 9(6):405-413; Ehard, H. et al., 1976, *Z. Rheumatol.* 35(9-10):324-336 and Russell, R., et al., 1981, *Scand J. Gastroenterol Suppl.* 67:215-217.

Examples of thrombotic animal models include, but are not limited to those in rats (Ravanat, C., et. al., *Thromb. Haemost.* 83:327-33 (2000)), rabbits (Zhao, et al., *Brain Res.* 902:30-9 (2001)), dogs (Bernat A., 1999, et. al., *J. Cardiovasc. Pharmacol.* 33:897-904), and baboons (Kruithof, E. K., 1997, et. al., *Thromb. Haemost.* 77:905-10).

In a preferred embodiment, the effective amount of salicylic acid administered to a patient in need thereof is about 100 to 200 µg/ml. In another preferred embodiment, the effective amount of acetylsalicylic acid administered to a patient in need thereof is about 600 µg/ml. In another embodiment, the effective amount of acetylsalicylic acid administered to a patient in need thereof is about 0.75 to 1.5 grams/day.

In particularly preferred embodiments, the effective amount of aspirin administered to a patient to treat or manage an ischemic event or a transient ischemic attack is 50-325 mg/day. In another preferred embodiment, the effective amount of aspirin administered to a patient to treat or manage a suspected myocardial infarction is 160-162.5 mg/day for 60 days. In another preferred embodiment, the effective amount of aspirin, administered to a patient to treat, manage or prevent a recurrence of myocardial infarction, unstable angina pectoris, chronic stable angina pectoris, or coronary artery bypass grafting surgery is 75-325 mg/day indefinitely. In another preferred embodiment, the effective amount of aspirin administered to a patient to improve the therapeutic outcome after a carotid endarterectomy is 80-650 mg, twice daily. In another preferred embodiment, the effective amount of aspirin administered to a patient to treat, manage or prevent rheumatoid arthritis, arthritis, osteoarthritis, or pleurisy is 3 g/day, initially. In another preferred embodiment, the effective amount of aspirin administered to a patient to treat, manage or prevent juvenile rheumatoid arthritis is 90-130 mg/kg/day. In another preferred embodiment, the target level in the blood plasma of a patient.

In preferred embodiment, the effective amount of stabilized TAFIa is an amount which results in TAFI plasma levels in the patient's blood of 0.01-20 µg/ml, preferably between 3-7 µg/ml, most preferably between 0.01-10 µg/ml.

In a preferred embodiment, the effective amount of other compounds of the invention are 50 mg/day to 5,000 mg/day.

The following examples are offered by way of illustration, not limitation.

EXAMPLES

Example 1

TAFIa Inhibition by Acetylsalicylic Acid, Salicylic Acid and Salicyluric Acid

Materials. TAFI was purchased from Hematological Associates (Essex Junction, Vt.) and TAFIa (3874TAFIa) was from American Diagnostica Inc. (Greenwich, Conn.). Carboxypeptidase activity of TAFIa was determined using ACTI-FLUOR™ TAFI (#874FX) a fluorescence-based assay from American Diagnostica (Greenwich, Conn.). ASA, SA and SU were obtained from Sigma Chemical Co. (St. Louis, Mo.).

Results. The present inventors have made the surprising discovery that ASA, SA and SU may shift the hemostatic balance toward a profibrinolytic state by inhibition of TAFIa, the major regulator of fibrinolysis. TAFIa was incubated with various concentrations of ASA, SA and SU for one hour, at room temperature. Residual TAFIa activity was measured using ActiFLUOR TAFIa. ASA, as well as SA and SU, directly inhibited the carboxypeptidase activity of TAFIa (FIG. 1). The rank order of potency was SU>SA>ASA, indicating that the metabolites of ASA are more potent inhibitors than ASA itself. Interestingly, other NSAIDS, such as ibuprofen and acetominophen, had little inhibitory effect on TAFIa activity (see FIG. 4). The inhibition of TAFIa by the salicylates was found to be non-competitive (see FIG. 4), suggesting that they interact with TAFIa outside the catalytic site of the enzyme. Catella-Lawson and coworkers recently reported that ibuprofen, taken prior to aspirin, blocks the irreversible inhibition of COX-1 by aspirin and abrogates the anti-platelet activity of aspirin. Catella-Lawson, F. et al., 2001, *N. Engl. J. Med.* 345(25):1809-17. Since ibuprofen has little effect on TAFI, it was reasonable to conclude that ibuprofen taken prior to aspirin would not block the profibrinolytic activity of aspirin caused by TAFI inhibition.

Significant inhibition of TAFI activity occurs-around 100 to 200 µg/ml of SA and SU and 600 µg/ml for ASA (FIG. 1). Pharmacokinetic studies show that the concentrations of ASA and its metabolites, SA and SU, required to inhibit TAFI are readily achieved in plasma during high dose aspirin therapy (0.75-1.5 grams per day). Thus, bleeding complications of aspirin associated with physiologically high plasma concentrations of ASA, SA and SU correlate with inhibition of TAFI activity.

Figure 4:
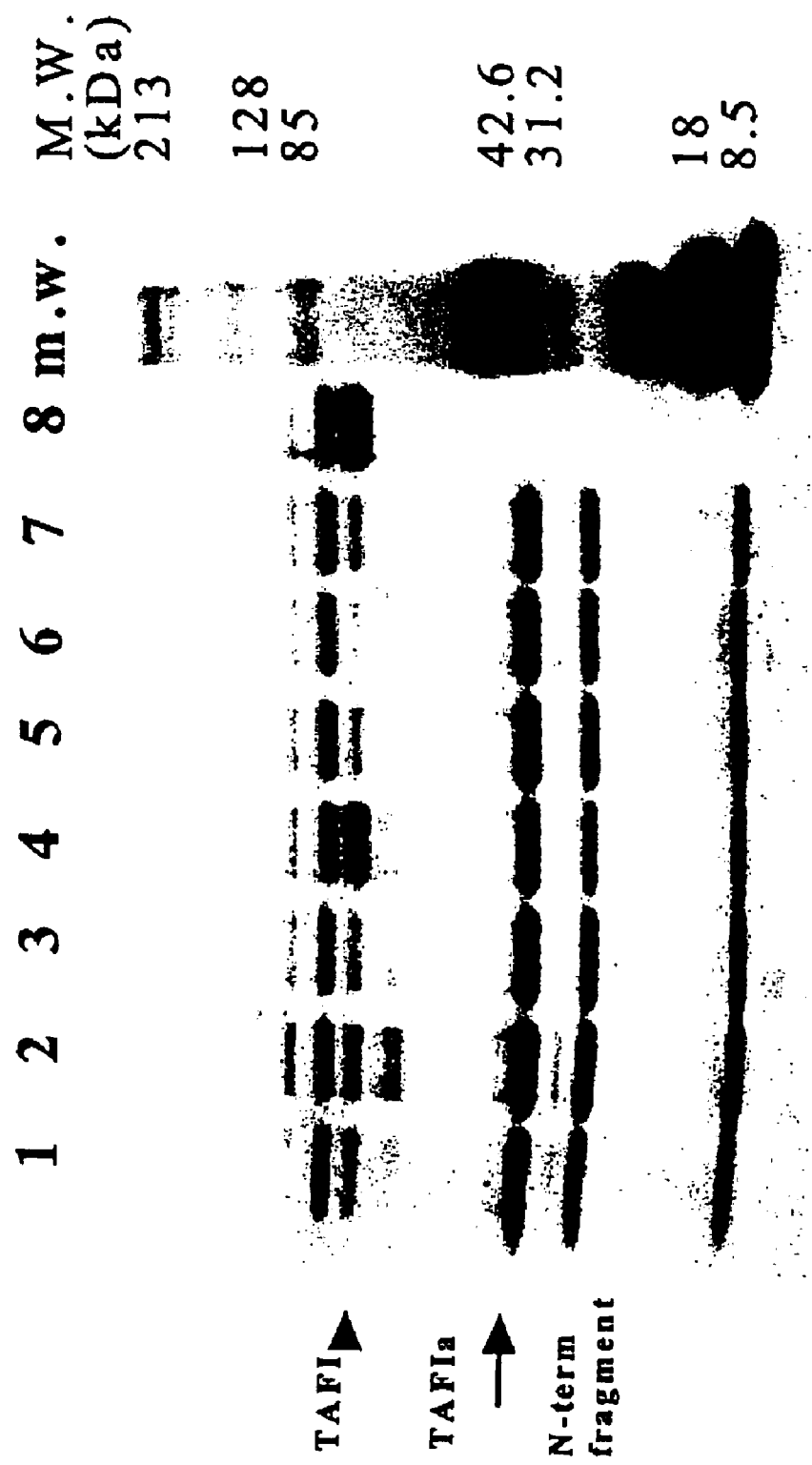
FIG. 4 shows TAFI activation by thrombin/thrombomodulin in the presence of various compounds. After 20 minutes, aliquots were removed and analyzed by SDS-PAGE. Lane 1. Acetylsalicylic acid; 2. Salicylic acid; 3. 4-hydroxybenzoic acid; 4. 2-hydroxybenzoic acid (salicyluric acid); 5. Ibuprofen; 6. Acetominophen; 7 Control with no addition; 8. TAFI. The results in FIG. 4 indicate that the salicylic acid and 2-hydroxybenzoic acid (salicyluric acid) inhibit the activation of TAFI. Interestingly, ASA and the other salicylate compounds tested did not appear to have a significantly effect on the rate of activation of TAFI by thrombin/thrombomodulin. Without being bound by any theory, these results, suggest that SA ad SU directly blocks the activation site of TAFI or indirectly blocks TAFI activation possibly through conformational effects upon binding to TAFI.
Figure 5:
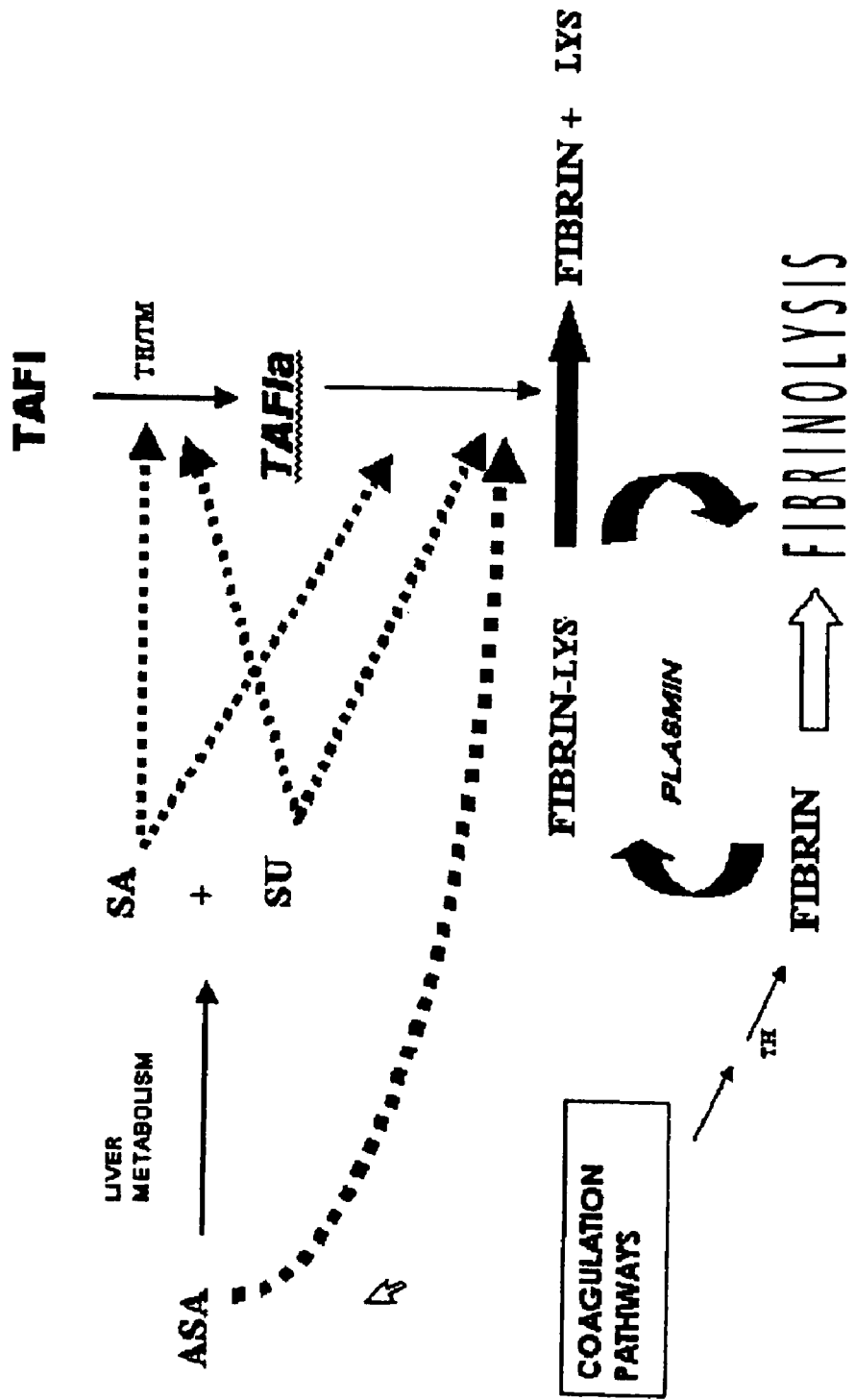
FIG. 5 is a schematic illustration of the mechanism of TAFI inhibition of fibrinolysis.
Figure 6:
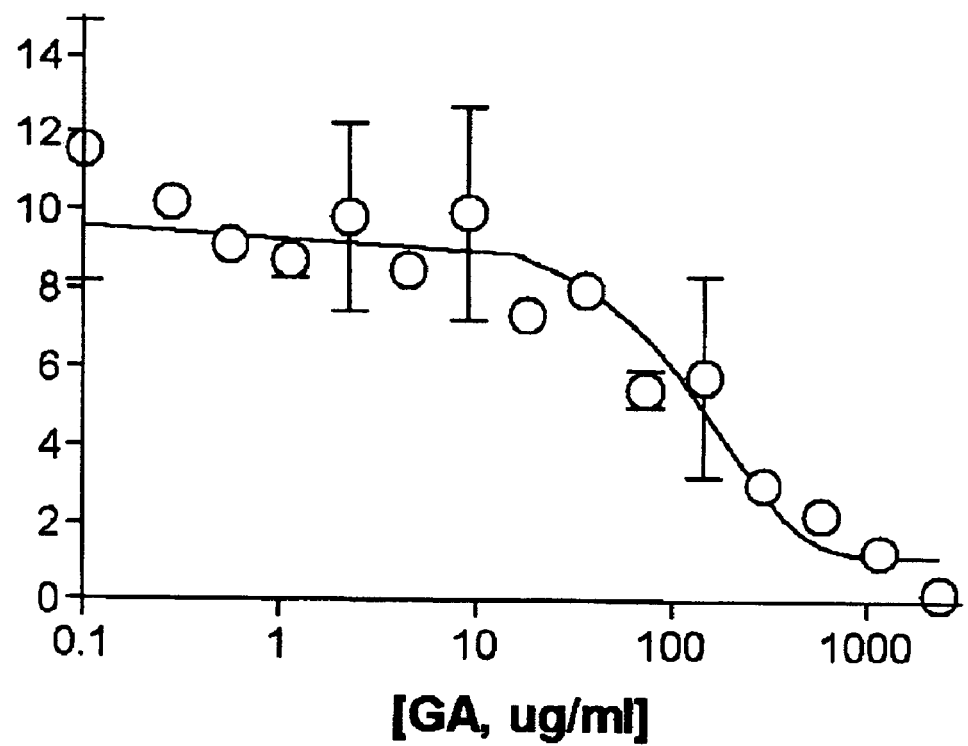
FIG. 6 shows competitive inhibition of TAFIa by gentisic acid. Different concentrations of gentisic acid (GA) were incubated with TAFIa and Actichrome 874 TAFI Developer. TAFI activity (Vmax) was determined.

The results in FIG. 4 indicate that physiological concentrations of SA and SU also inhibit activation of TAFI to TAFIa by thrombin/thrombomodulin. Not only, then, do SA and SU inhibit enzyme activity, they also retard the generation of TAFIa. Without being bound by any theory, this provides a dual mechanism by which fibrinolysis is enhanced during high dose aspirin therapy. The proposed pathways by which aspirin and its major metabolites SA and SU enhance fibrinolysis through inhibition of TAFI is presented in FIG. 5. Undas recently showed that thrombin generation at the wound site is also inhibited by aspirin. Undas et al., 2001, *Blood* 98:2423-31. This suggests that aspirin therapy may also affect other components of the coagulation pathway.

Example 2

Synthesis of Chemical Compounds

This example provides pathways for synthesizing some of the compounds to be tested in the assay described in Example 3.

Synthesis of 2-(2-hydroxybenzoylamino)ethyl N-(3-aminopropyl)carbamate a278R)

N-(2-Hydroxyethyl)-2-hydroxybenzamide (5.43 g, 30 mM) was dissolved in dry pyridine (40 ml). The reaction mixture was vigorously stirred at 0° C. while p-nitrophenyl chloroformate (9.0 g, 45 mM) was added in portions over 30 min. The reaction mixture was stirred at r.t. for 20 hrs and the solvent was removed under vacuum. The residue was dissolved in CHCl$_3$ and chromatographed on a silica gel column with CHCl$_3$:EtOH=99:1. The fraction preceding the yellow zone was collected and evaporated to dryness to give O-(2-hydroxybenzoylamino) ethyl O'-(4-nitrophenyl)carbonate as a colorless solid (8.0 g). O-(2-hydroxybenzoylamino)ethyl O'-(4-nitrophenyl)carbonate (345 mg) was dissolved in dry DMF (2 ml), 3-azidopropylamine (500 mg, 5 mM) was added and the reaction mixture was stirred at r.t. for 48 hrs. The volatiles were removed under vacuum (0.2 mm Hg) and the residue was chromatographed on silica gel column with hexane:ethyl acetate=3:1 to 2:1. The only UV fluorescent zone afforded after removal of the solvent under vacuum 2-(2-hydroxybenzoylamino) ethyl N-(3-azidopropyl)carbamate (220 mg) as a colorless solid.

2-(2-Hydroxybenzoylamino)ethyl N-(3-azidopropyl)carbaniate (128 mg) was dissolved in methanol (15 ml), 10% Pd/C (140 mg) was added and the reaction mixture was vigorously stirred while hydrogen was bubbled at r.t. for 3 hrs. The catalyst was filtered off and the methanol removed under vacuum to provide 2-(2-hydroxybenzoylamino)ethyl N-(3-aminopropyl) carbamate (88 mg) as a colorless oil.

Synthesis of 2-(2-hydroxybenzoylamino)ethyl N-2-[2,3-bis(benzyloxy)benzoylamino]ethyl carbamate (LT32)

2-[2,5-Bis(benzyloxy)benzoylamino]-ethylamine (564 mg, 1.5 mM) and O'-[2-(2-hydroxybenzoylamino)-3-phenylpropyl]-O'-(4-nitrophenyl)carbonate (522 mg, 1.5 mM) were dissolved in dry DMF (4 ml) and the mixture was stirred at r.t. for 24 hrs. The solvent was removed under vacuum and the residue was chromatographed on a silica gel column with hexane:ethyl acetate=50:50, 33:66, 20:80. The fractions containing the product were combined, the solvent removed under vacuum and the residue was recrystallized from hexane:ethyl acetate and once again from ethyl acetate to provide 2-(2-hydroxybenzoylamino) ethyl N-2-[2,3-bis(benzyloxy)benzoylamino]ethyl carbamate (500 mg) as a colorless solid.

Synthesis of N-[(S)-1-hydroxy-3-phenyl-2-propyl]-2,5-dihdroxybenzamide (JV59)

In a flask equipped with a reflux condenser and a magnetic stirring bar are dissolved the methyl 5-benzyloxy-2-hydroxybenzoate and one equivalent of 2-(S)-amino-3-phenyl-1-propanol in dry dimethyl formamide. The flask is immersed in an oil bath at 75° C. and left to stir for 72 hours. The solvent is evaporated and the residue is isolated-through the use of a silica gel column using a mixture of ethyl acetate and hexane as eluent. In this fashion is obtained in 50% yield, N-{(S)-1-hydroxy-3-phenyl-2-propyl}-5-benzyloxy-2-hydroxybenzamide.

In a flask equipped with a magnetic stirring bar and a rubber septum is dissolved the N-{(S)-1-hydroxy-3-phenyl-2-propyl}-5-benzyloxy-2-hydroxybenzamide in methanol. Nitrogen is bubbled through the solution and 10% Pd on charcoal is added. After flushing with nitrogen, the suspension is placed under hydrogen atmosphere and stirred for 2 hours. The suspension is flushed with nitrogen and filtered and rinsed over Celite. The filtrate is concentrated under vacuum. In this fashion is obtained N-{(S)-1-hydroxy-3-phenyl-2-propyl}-2,5-dihydroxybenzamide (85%).

Example 3

Measurement of Compounds for TAFI-Iinhibition

The activity of the chemical compounds was assessed in the ActiScreen® TAFI HTS assay, the principle of which is shown below.

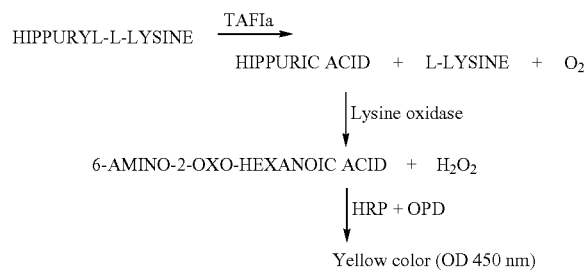

The assay is run by mixing TAFIa and test compound in microtiter plate wells. "TAFI developer" is then added to start the reaction which is run at room temperature. The TAFI developer is formulated with hippuryl-L-lysine, lysine oxidase, horseradish peroxidase and ortho-phenylene-diamine. Hippuryl-L-lysine is converted by TAFIa to hippuric acid and L-lysine. Lysine-Oxidase (LOX) converts the lysine to 6-amino-2-oxo-hexanoic acid and hydrogen peroxide. The hydrogen peroxide is used along with ortho-phenylene-diamine (POD) as substrate for horseradish peroxidase. The reaction produces a yellow color that was monitored for Vmax in a spectrophotometer (SpectroMax 190, Molecular Devices, Sunnyvale, Calif.) in the kinetic mode at 450 nm.

The assay can also be run as an endpoint reaction in which the enzymatic reaction is stopped at a selected point in time with 0.5 M sulphuric acid. The resulting color is read at 490 nm. A TAFI inhibitor will block the first reaction in the cascade in which TAFIa converts hippuryl-L-lysine to hippuric acid and lysine, which finally results in a decrease in Vmax or OD 490 nm relative to control reaction without addition of test compound. The assay has been designed to be run in final concentrations of DMSO of up to 20%. A known inhibitor of TAFIa carboxypeptidase activity, potato tuber carboxypeptidase inhibitor (PTCI), is used as a positive control.

Figure 7:
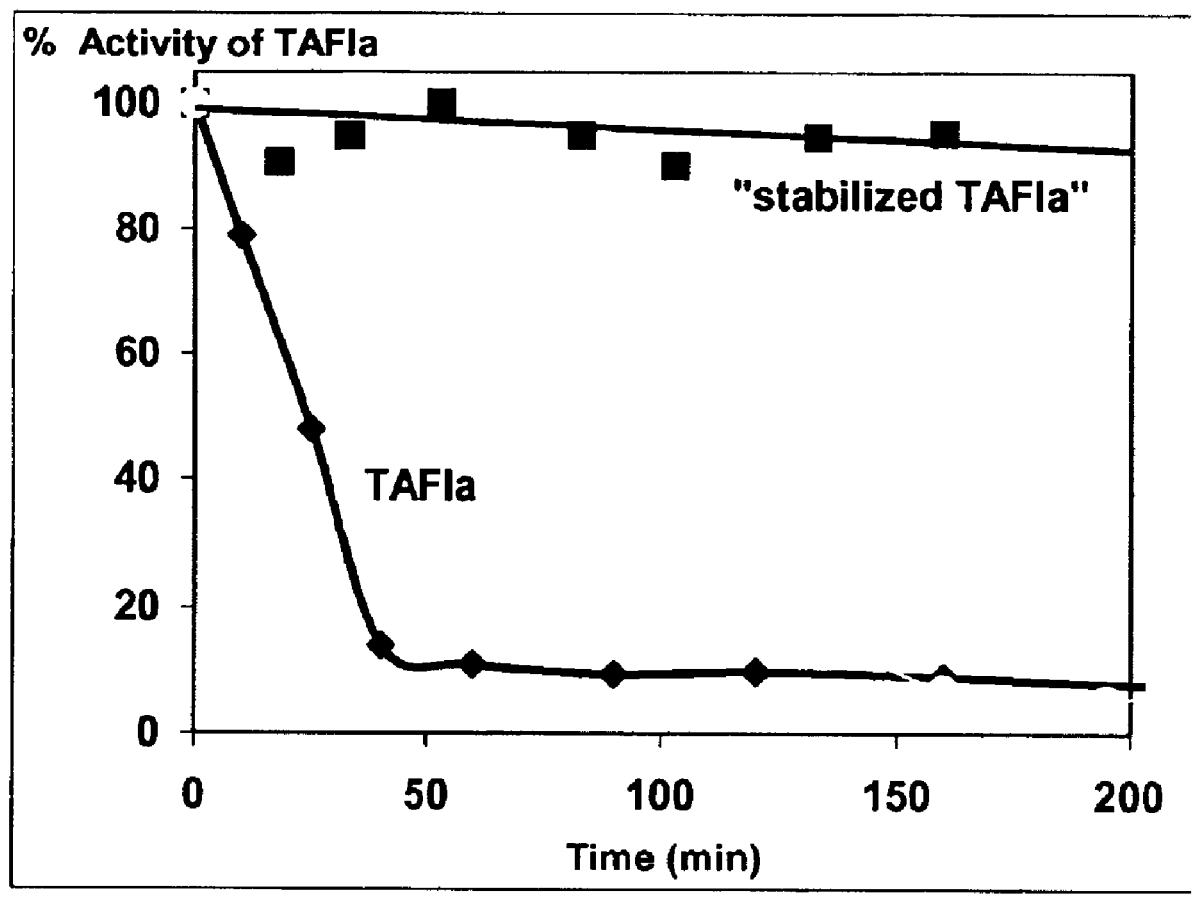
FIG. 7 shows increased-stability at room temperature of stabilized TAFIa compared to conventional TAFIa.

The TAFIa used in the ActiScreen HTS assay is a specially formulated preparation from native human TAFI which is highly more stable than TAFIa prepared by conventional methods. The enhanced ability of stabilized TAFIa at room temperature compared to conventional TAFIa preparation is shown in FIG. 7.

Example 4

Screening Chemical Compound Libraries

Positive hits were selected based upon the ability of compounds to inhibit carboxypeptidase activity of TAFIa, as measured in the ActiScreen assay. The major criterion for selection of "hits" was based on their potency, as determined by the concentration of compound that inhibits the activity of TAFIa in the Actiscreen TAFI assay by 50% ("IC50").

Positive hits identified with the ActiScreen TAFI assay were dereplicated to ensure that the inhibition of color development is due to blocking of the first reaction of the linked enzyme system catalyzed by TAFIa and not to inhibition of LOX or HRP. Dereplication was performed by testing whether the lead test compounds inhibit the reaction of LOX/HRP with d/l -lysine as the substrate. All compounds were tested at concentrations 5-10 times greater than their IC50 values determined for TAFI.

Figure 8:
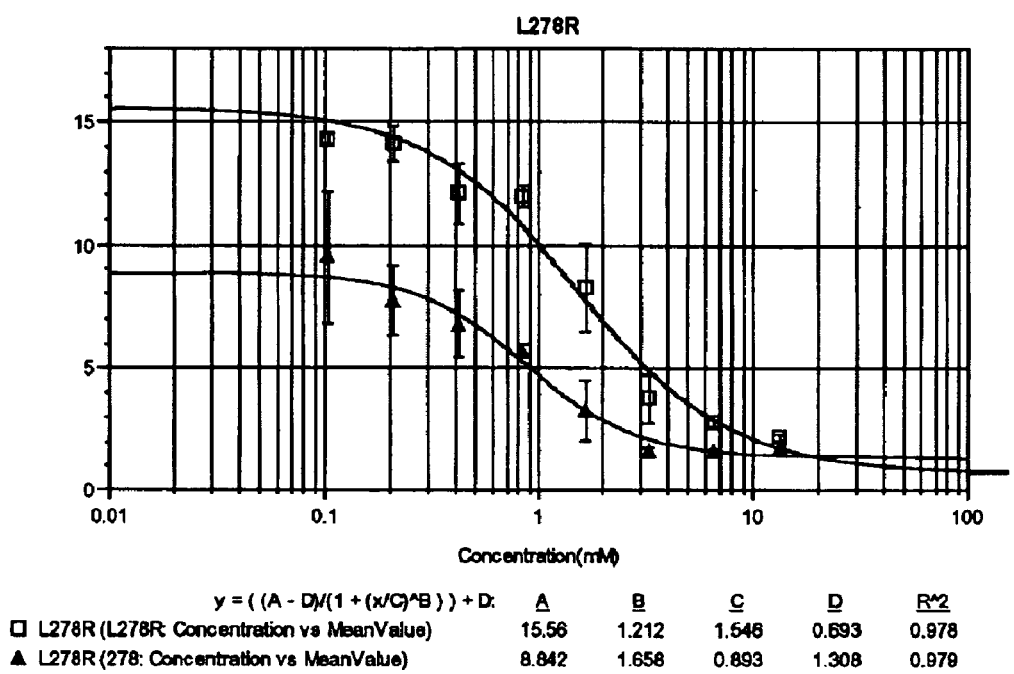
FIG. 8 shows concentration-dependent inhibition of TAFIa activity by L278 using two methods. Method 1: no preincubation (□); Method 2. Preincubation for 1 hour at 4° C. prior to assay (▲). Curve fitting was performed using Softmax Pro program.

Using this methodology, the inventors have screened hundreds compounds and identified structural motifs that are associated with inhibition of TAFIa carboxypeptidase. One class of TAFI inhibitors is represented by the compound L278R, which inhibits TAFIa via two mechanisms. When the assay was performed as described in Example 3, L278R appeared to be a competitive type inhibitor of TAFI with an IC50 value of 1.54 mM. However, when TAFIa was preincubated with L278R for 1 hour at 4° C. prior to testing for carboxypeptidase activity using ActiScreen TAFI assay, the IC50 shifted to a significantly lower value 0.89 mM (FIG. 8). This shows that L278R also can act as a non-competitive-type inhibitor of TAFI. The structure of L278R is shown below.

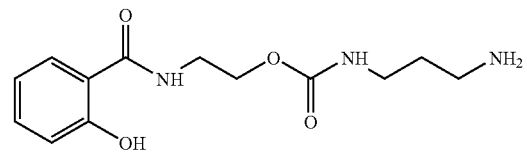

Figure 9:
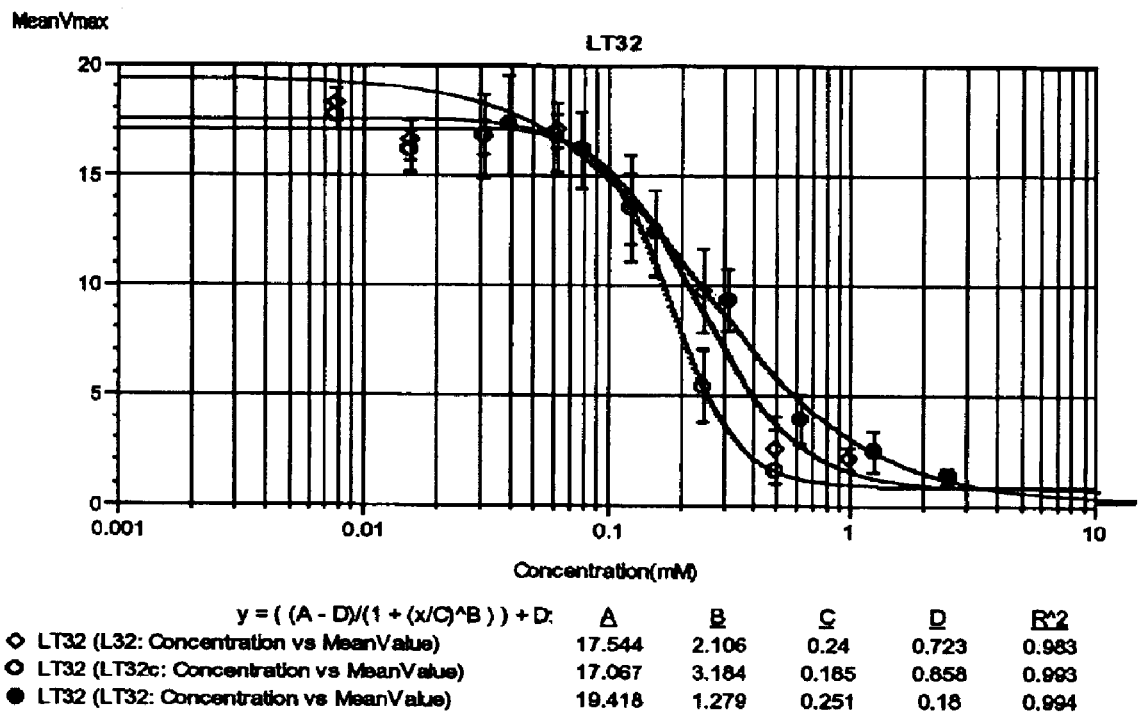
FIG. 9 shows concentration-dependent inhibition of TAFIa activity by LT32. The results from three independent experiments are shown. Curve fitting was performed using Softmax program.
Figure 10:
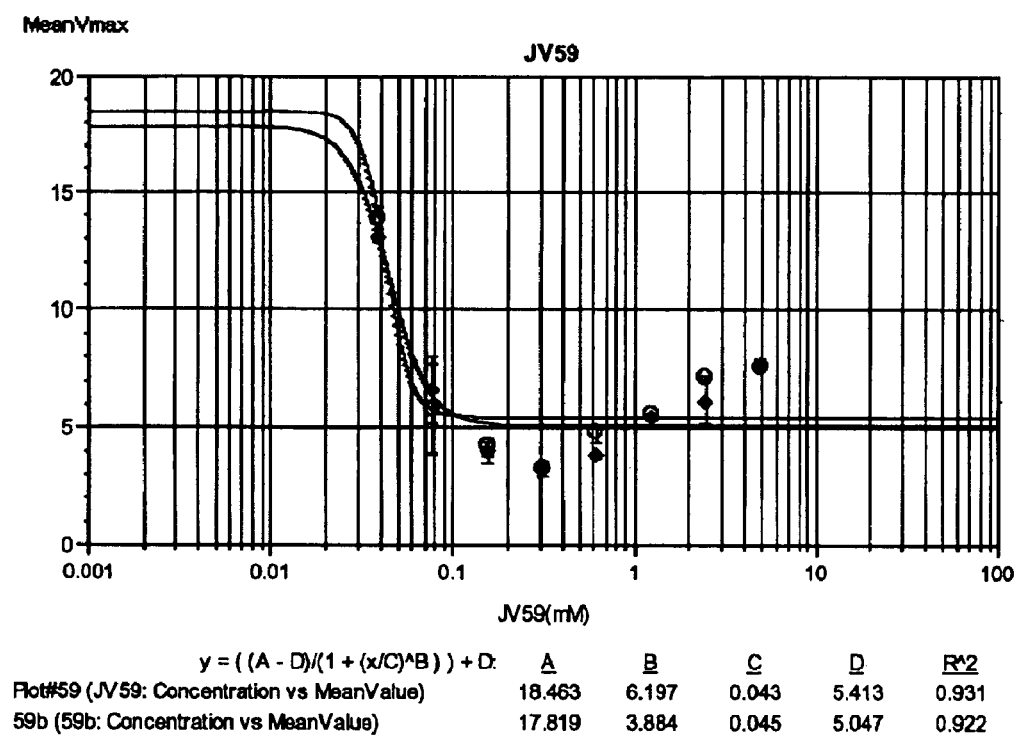
FIG. 10 shows concentration-dependent inhibition of TAFIa activity by JV59. The results from two independent experiments are shown. Curve fitting was performed using Softmax program.

Another class of TAFI inhibitors is represented by the compound LT32. The IC50 determined for LT32 is 225 µM. LT32 is a competitive inhibitor of TAFIa (FIG. 9). The structure of LT32 is shown below.

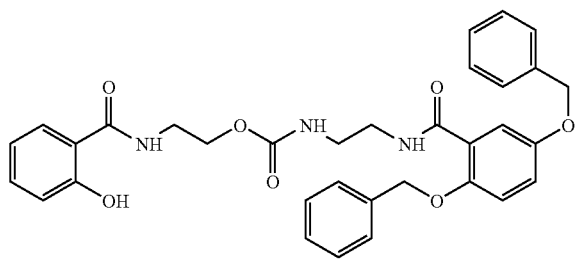

The compound JV59 has structural features in common with the class of compounds to which LT32 belongs. JV59 scored as a potent hit in the screening assay, with an IC50 of 44 μM. The structure of JV59 is shown below.

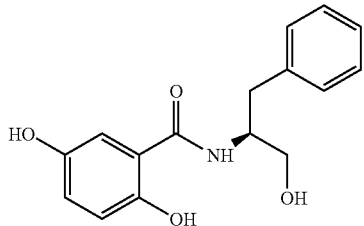

Compounds L278R and LT32 were tested in the dereplication assay, described above. Neither of the compounds had a significant effect on the reaction rate (Vmax) of LOX/HRP with lysine. The inventors conclude that these compounds inhibit TAFIa and not LOX/HRP.

L278R was also tested for specificity against Carboxypeptidase N(CPN). CPN is the constituitively active carboxypeptidase B-like enzyme in plasma. In this study, pooled normal human plasma (PNP) was used as the source of CPN. The specificity studies were performed by adding PNP (1:10), ActiScreen developer and serially diluted test compound into microtiter wells. Inhibition of color development was an indication of inhibitory activity towards CPN. The results indicated that L278R did not inhibit CPN, demonstrating that it is specific for TAFIa.

Example 5

Screening Compounds for Analgesia

A test compound, such as a derivatized analgesic, is selected. The compound is incubated with TAFIa for 30 minutes and TAFIa inhibition is measured using a fluorometric in vitro assay as described herein. If the compound shows little or no TAFIa inhibition, then the test compound is administered to a rat prior to conducting a hotplate assay as described herein. If the latency to the lick is increased by the test compound, then a non-inhibitor of TAFIa with potential analgesic activity is identified. The identified compound may then be tested for other activities, e.g., antipyretic activity.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled

We claim:

1. A method of identifying a compound which possesses (i) at least one aspirin activity selected from the group consisting of COX-1 inhibition and COX-2 inhibition, and (ii) no TAFIa-inhibition, comprising the steps of:
   a) exposing TAFIa to the test compound;
   b) measuring carboxypeptidase activity of TAFIa in the presence of and in the absence of the test compound;
   c) determining whether the test compound inhibits carboxypeptidase activity of TAFIa and/or inhibits TAFI activation by measuring the level of carboxypeptidase activity of TAFIa during exposure to the test compound; and
   d) determining whether at least one aspirin activity is retained by the test compound, thereby identifying a compound that possesses at least one aspirin activity but not TAFIa-inhibitory activity.

2. The method of claim 1, wherein the aspirin activity is COX-2 inhibition.

3. The method of claim 1, wherein the aspirin activity is COX-1 inhibition.

4. A method of evaluating inhibition of TAFIa activity by a test compound, in comparison with aspirin, salicylic acid, salicyluric acid or gentisic acid, comprising the steps of:
   a) exposing TAFIa to the test compound;
   b) measuring carboxypeptidase activity of TAFIa in the presence of and in the absence of the test compound;
   c) measuring the level of inhibition of carboxypeptidase activity of TAFIa by the test compound;
   d) exposing TAFIa to aspirin, salicylic acid, salicyluric acid or gentisic acid;
   e) measuring the level of inhibition of carboxypeptidase activity of TAFIa by aspirin, salicylic acid, salicyluric acid or gentisic acid; and
   f) comparing the level of inhibition of carboxypeptidase activity of TAFIa by the test compound to the level of inhibition of carboxypeptidase activity of TAFIa by aspirin, salicylic acid (SA), salicyluric acid (SU) or gentisic acid,
   thereby determining whether the test compound inhibits TAFIa activity more or less than aspirin, salicylic acid, salicyluric acid or gentisic acid.

5. The method of claim 4, wherein step (a) further comprises preincubating TAFIa and the test compound for at least about 20 minutes.

6. The method of claim 4, wherein (b), (c), and (e) are carried out using a clot lysis assay.

7. The method of claim 4, wherein (b), (c), and (e) are carried out using a fibrinogen assay.

8. The method of claim 4, wherein (b), (c), and (e) are carried out using a plasminogen capture assay.

9. The method of claim 4, wherein (b), (c), and (e) comprise using a fluorescent based assay.

* * * * *